(12) United States Patent
Shadduck

(10) Patent No.: US 6,679,879 B2
(45) Date of Patent: Jan. 20, 2004

(54) ELECTRICAL DISCHARGE CATHETER SYSTEM FOR EXTRACTING EMBOLI IN ENDOVASCULAR INTERVENTIONS

(76) Inventor: John H. Shadduck, 1490 Vistazo West, Tiburon, CA (US) 94920

( * ) Notice: Subject to any disclaimer, the term of this patent is extended or adjusted under 35 U.S.C. 154(b) by 77 days.

(21) Appl. No.: 09/727,648

(22) Filed: Nov. 30, 2000

(65) Prior Publication Data

US 2002/0095147 A1 Jul. 18, 2002

Related U.S. Application Data

(60) Provisional application No. 60/225,990, filed on Aug. 16, 2000.

(51) Int. Cl.[7] .............................................. A61B 18/18
(52) U.S. Cl. ......................... 606/41; 607/104; 607/105
(58) Field of Search ............................ 606/41, 45, 46, 606/47, 48, 49, 50; 607/101, 102, 103, 104, 105; 604/101.05

(56) References Cited

U.S. PATENT DOCUMENTS 5,938,660 A * 8/1999 Swartz et al. ................. 606/45
6,022,336 A * 2/2000 Zadno-Azizi et al. .. 604/101.05
6,311,692 B1 * 11/2001 Vaska et al. ................. 128/898

* cited by examiner

Primary Examiner—Linda C. M. Dvorak
Assistant Examiner—Kenneth G Schopfer

(57) ABSTRACT

A catheter system for removing occlusive materials from a targeted endoluminal site, such as a vascular graft. The catheter system utilizes an electrical source and a controller to deliver sequences of very small electrical discharges between paired electrodes in a fluid-jet arrangement (i) to cause high fluid flow velocities in the catheter's fluid extraction pathway based on Bernoulli's Law of Pressure Differential, (ii) to create a selected level of turbulent fluid flows within the targeted site to remove occlusive material from the vessel walls and to thereafter suction fluids and entrained embolic particles into the extraction pathway, and (iii) to emulsify any embolic particles having a cross-sectional dimension larger than a couple of hundred micrometers to allows passage of the embolic particles through the elongate catheter to the catheter handle.

15 Claims, 20 Drawing Sheets

ELECTRICAL DISCHARGE CATHETER SYSTEM FOR EXTRACTING EMBOLI IN ENDOVASCULAR INTERVENTIONS

CROSS-REFERENCE TO RELATED APPLICATIONS

This application claims benefit of Provisional U.S. Patent Application Ser. No. 60/225,990 filed Aug. 16, 2000 titled Electrical Discharge Thrombolysis Catheter and Method Based on Bernoulli's Law of Pressure Differential, which is incorporated herein by this reference.

BACKGROUND OF THE INVENTION

1. Field of the Invention

The present invention relates to medical devices and techniques, and more particularly to catheter systems and medical interventions for treating elongate occluded regions in vascular coronary artery grafts. The inventive catheter system is adapted for capturing and extracting embolic fragments that typically develop in any endovascular intervention. The catheter system utilizes sequences of microelectrical discharges in catheter channels to (i) remove occlusive materials from the vessel walls around a treatment site; (ii) generate fluid extraction forces; and (iii) to emulsify or ablate large fragments of dislodged occlusive materials, thus allowing the emboli extraction system to be fabricated in a very small diameter catheter.

2. Description of Related Art

Vascular grafts in coronary artery bypass procedures (CABG) often become occluded over time by plaque, thrombus, or other deposits that can significantly reduce blood flow through the graft. In such bypass grafts, the occlusions are frequently diffuse and elongate making medical interventions problematic. It has been found that conventional treatments of such saphenous vein bypass grafts (e.g., balloon angioplasty, atherectomy, etc.) can cause significant risk of embolisms by dislodging occlusive material that can then migrate downstream. If an embolism occurs at a critical location in the patient's circulatory system, a permanent injury or even death may occur.

The risk of embolism also is prevalent in medical interventions to treat occlusions in native vessels. For example, it is known that stent deployment often leads to the dislodgement of embolic fragments. In some occlusions in native vessels, such as the carotid arteries, the risks of emboli reaching the brain are so significant that catheter-based treatments of such occlusions are rarely practiced.

Various endovascular catheter systems have been developed for treating occluded vascular grafts and for capturing embolic material during the intervention. As an example, it is believed that the leading candidate for commercialization is an assembly of concentric catheter sleeves that allows for irrigation and aspiration of fluids from a vessel that is temporarily blocked upstream and downstream by inflatable balloons, using an assembly of catheter sleeves as depicted in FIG. 1A. The irrigation and aspiration systems provide a looped flow of fluid (e.g., saline) through inflow and outflow pathways between the various catheter sleeves wherein the pathways communicate with external positive and negative pressure sources. The arrangement of concentric catheters of FIG. 1A was disclosed by Zadno-Azizi et al. in U.S. Pat. No. 6,022,336. In using the type of catheter assembly just described, the physician is supposed to use the intermediate catheter to carry an additional functional component for performing a medical intervention, such as an angioplasty or any other form of treatment. Such treatments may dislodge emboli between the upstream and downstream balloons. The contemporaneous in-and-out irrigation and aspiration of fluids is then intended to flush any embolic particles from the treatment region between the balloons. In order understand the shortcomings of this type of catheter assembly that relies on external irrigation ration systems, it first is necessary to describe the operating parameters of a typical intervention— in terms of (i) the dimensions of the operating space within the vessel and (ii) the dimensions of potential emboli that must be captured and removed The principal difficulty in designing an interventional catheter system for controlling emboli in vascular grafts relates to the small size of a typical bypass graft. A saphenous vein graft in a CABG procedre has a lumen diameter ranging between about 3 mm. and 4 mm., although some grafts can range to about 5 mm. to 6 mm. Thus, the outside diameter of a catheter system must be small enough to navigate 3 mm. or 4 mm. lumens, and preferably much smaller to treat vessels with smaller lumens, and to pass through the partially occluded lumen of a graft.

The other important consideration in such an intervention treatment relates to the crosssectional dimensions of potential embolic fragments. It is postulated that the most dangerous emboli have cross-sections ranging from greater that a few hundred micrometers ($\mu$m), for example, from about 200 $\mu$m or 300 $\mu$m to about 600 $\mu$m Certainly, smaller emboli are common and also are targeted for capture and removal— but particles in the range of 50 $\mu$m or less may not prove as dangerous as larger emboli since they may pass through the blood stream. Therefore, the catheter system of the type shown in FIG. 1A ideally would have an emboli extraction pathway with a cross-section capable of extracting 500 $\mu$m to 600 $\mu$m particles without clogging.

As one can easily understand, it is problematic to construct a catheter assembly that has an outer diameter of significantly less than about 3 mm. and still provide an inner lumen diameter of 600 $\mu$m or more for extracting emboli— particularly when the catheter will require as many as four other inflow/outflow channels or lumens. A second channel will be required for irrigation; third and fourth channels will be required for inflating the proximal and distal balloons; and in most cases, a fifth channel will be required to accommodate a guidewire. Another sixth channel within the working end will be required if the intervention is time-consuming so that blood perfusion around the balloon assembly is needed. Even if the desired functionality associated with the above described five or more lumens could be packaged in a 3.0 mm. cross-section catheter, the overall system still would be much larger than optimal. As can be seen in FIG. 1A, the external dimension of the outer catheter is too large to for easy navigation through a typical blood vessel targeted for treatment. The system of FIG. 1A also has several other serious drawbacks, as will be described next.

In order to better understand the functionality of the prior art catheter assembly of FIG. 1A, it is necessary to explain the parameters for providing "optimized paths for irrigation and aspiration" as proposed in U.S. Pat. No. 6,022,336. Further, it is necessary to analyze real-world dimensions of a typical treatment space. For this reason, TABLE A is provided below, which along with FIGS. 1A & 1B, describe the practical dimensions of an exemplary catheter assembly of the type proposed in U.S. Pat. No. 6,022,336.

The figures in TABLE A are listed in or $\mu$m (i.e., micrometers with an approximation in inches) to allow reference to emboli dimensions which are typically given in micrometers. For the catheter assembly of FIGS. 1A–1B to function optimally in capturing and removing emboli, there are essentially three dimensional factors that must be considered: (i) the radial dimension of the free space between the catheter's exterior and the vessel wall to allow fluid flows therein to remove, capture and entrain emboli; (ii) the cross-sectional dimension of the fluid irrigation pathway within the catheter assembly to allow sufficient fluid inflows; and (iii) most importantly, the cross-sectional dimension of the extraction pathway within the catheter assembly to allow embolic fragment to flow therethrough to the remote handle of the catheter.

As discussed above, consider that the typical vessel lumen targeted for treatment is either 3 mm. or 4 mm. (i.e., 3000 $\mu$m to 4000 $\mu$m) as indicated in TABLE A The dimensions of the exemplary catheter assembly are best aggregated from the inner catheter outwardly. The inner catheter sleeve indicated at 4 in FIGS. 1A–1B has a lumen diameter of 500 $\mu$m to place over a typical 0.014" guidewire. As can be seen in FIG. 1A, this catheter sleeve 4 requires a balloon inflation lumen in a thickened wall portion that results in an outer catheter sleeve diameter of about 960 $\mu$m. FIG. 1A shows the irrigation pathway comprising by the free space between the inner catheter sleeve 4 and the intermediate catheter sleeve 5, which is best measured by a difference ($\Delta$) in the radial dimension (or radius) between the respective sleeve diameters. In this exemplary embodiment, the radial $\Delta$ is 120 $\mu$m which can provide sufficient cross-section area for projected fluid inflow rates. The intermediate catheter sleeve 5 thus has an inner diameter of about of 1200 $\mu$m. The very thin wall around the lumen of the catheter (e.g., about 200 $\mu$m) results in an outer diameter of 1600 $\mu$m for the intermediate catheter sleeve 5.

In the assembly of FIG. 1A, the aspiration or extracion passageway must be located between the outer catheter sleeve 6 and the intermediate catheter sleeve 5. Assume that the outer diameter (OD) of the outer catheter sleeve 6 is at a maximum possible dimension, for example 2800 $\mu$m which is close to the diameter of the lumen targeted for treatment. Still referring to FIG. 1A, the outer catheter sleeve 6 further requires a balloon inflation lumen in a wall portion thereof resulting in a maximum inner sleeve diameter of about 2300 $\mu$m. Now, it can be seen that the radial $\Delta$ of the aspiration passageway in this embodiment is only about 350 $\mu$m radial $\Delta$ of only 350 $\mu$m. The outermost diameter of the catheter assembly cannot realistically be increased since it already is 2800 $\mu$m—close to the diameter of the vessel lumen targeted for treatment. TABLE A further shows that the free space on either side of the catheter assembly in the vessel lumen has a radial $\Delta$ of 350 $\mu$m to 1200 $\mu$m, for 3 mm. and 4 mm. vessels, respectively. This open dimension of the working space on one side of the catheter may be too small to carry large embolic fragments to the open end of the aspiration passageway. In any such cases that the emboli is not aspirated, the large emboli would remain in the vessel lumen after the downstream balloon is collapsed, and thereafter would be free to migrate downstream and cause an embolism.

Besides the fact that a 2.8 mm. catheter assembly of FIG. 1A cannot optimize dimensions for (i) the working space, (ii) the irrigation pathway, and (iii) the emboli aspiration pathway, there are several other technical reasons that limit the suitability of such a catheter assembly for containing and removing emboli. First the entire purpose of the catheter assembly of FIG. 1A is to provide the intermediate catheter 5 with additional medical intervention functionality, such as any angioplasty, stent delivery or atherectomy means. For example, if a typical balloon angioplasty system were added to the intermediate catheter 5, an additional high-pressure balloon inflation lumen would be required which would result in much thicker walls in the intermediate catheter, and correspondingly greater dimensions in the outer catheter (or lesser dimensions of the aspiration pathway). Similarly, if any other functional components were added to the intermediate catheter, its cross-section would be increased. Thus, in a real world fabrication of a working catheter assembly as shown in FIG. 1A, the free working space, the irrigation passageway and/or the aspiration passageway would be much further restricted by the increased cross-section of a true working intermediate catheter.

Second, the catheter's looped fluid flow from the irrigation-aspiration sources can function properly only with a balance of inflow and outflow pressure levels from the external sources used to circulate fluid through the working space. Such positive and negative pressures sources must be finely balanced so as to not cause overpressures in the working space. Any overpressure of about two to three times the normal intravascular pressure could rupture the vessel wall within the working space isolated between the balloons. It can be easily understood that the looped fluid flow—first

TABLE A

| vessel lumen diameter | outer body member | | intermediate body member | | inner body member | |
|---|---|---|---|---|---|---|
| | catheter OD | catheter ID | catheter OD | catheter ID | catheter OD | catheter ID |
| 4000 $\mu$m or 3000 $\mu$m | 2800 $\mu$m (+/−.120") | 2300 $\mu$m (+/−.082") | 1600 $\mu$m (+/−.062") | 1200 $\mu$m (+/−.048") | 960 $\mu$m (+/−.038") | 500 $\mu$m (+/−.020") |

| WORKING SPACE DIMENSION radial $\Delta$ between lumen ID and intermediate catheter OD | ASPIRATION PATHWAY DIMENSION radial $\Delta$ between outer catheter ID and intermediate catheter OD | FLUID INFLOW LUMEN radial $\Delta$ between intermediate catheter ID and inner catheter OD |
|---|---|---|
| 1200 $\mu$m (in 4000 $\mu$m lumen) 350 $\mu$m (in 3000 $\mu$m lumen) | 350 $\mu$m | 120 $\mu$m |

A number of important practical observations can be made from analyzing the data in TABLE A and FIGS. 1A–1B. Most important, many of the most dangerous embolic particles with large dimensions (e.g., 400 $\mu$m to 600 $\mu$m) could not be carried through the aspiration pathway which has a distally (inwardly) in the irrigation pathway and then outwardly (proximally) in the aspiration pathway—creates inertial forces. If the aspiration channel were suddenly blocked, significant overpressures would instantly build up in the working space. It firer can be seen that blockages of the aspiration channel of the catheter assembly of FIG. 1A are highly likely. As mentioned above, large emboli may not even pass through the aspiration channel; other smaller emboli may still clog the aspiration pathway since the shape of the concentric area around the intermediate catheter 5 will be in flux as the intermediate catheter sleeve flexes with the constraining bore of the outer catheter 6, which is indicated by the arrows in FIG. 1B. As can be understood from FIGS. 1A–1B, even slight changes in the crosssections of the irrigation and aspiration pathways will make it difficult to modulate pressures to maintain the looped circulatory flow at a particular pressure. More likely, there will be pressure spikes in the working space that could risk rupturing the vessel and risk the patient's health.

A third serious drawback of the catheter assembly of FIG. 1A relates to its lack of flexibility. Many, if not all, targeted sites will be found in vessels that are curved or even tortuous. Since the catheter assembly may substantially occupy the lumen of the vessel, and must flex, one side of the outer catheter sleeve 6 inevitably will be pressed against the vessel wall. Thus, the looped circulatory flows of fluids with the assembly of FIG. 1A will not typically cleanse fragments from the vessel wall portion that is pressed against the catheter. Due to the limited treatment time in which fluid flows about the working space (i.e., as little as 2 to 4 minutes since downstream blood flow is blocked by the balloon) there probably will be inadequate time to adjust the catheter in some way to insure that fluid flows reach all wall portions of the vessel. As mentioned previously, it would be possible to increase treatment times by adding a perfusion lumen. However, it would very difficult to carry blood through three different catheter sleeves and then around the paired occlusion balloons. Any such perfusion functionality would likely require a much larger assembly cross-section, which is not a realistic option.

The author believes that principles of irrigation and aspiration of fluids to remove emboli from an endovascular workspace are sensible. However, the prior art catheter assembly of FIG. 1A is best suited for larger vessels, for example, vessels having a lumen of about 5 to 6 mm. or larger.

What is needed is a catheter system for containing and removing emboli that has the following characteristics:

(i) a system that can be scaled down in cross-section to function in 2 mm. to 3 mm. lumens, or even smaller;

(ii) a system that can effectively remove large emboli—up to 600 micrometers in diameter or larger;

(iii) a system that eliminates any possibility of overpressure in an endoluminal working space;

(iv) an endovascular system that cooperates with related interventions (e.g., angioplasty or stent placement)

(v) an endovascular system that can remove any type of embolic material, from calcified fragments to thrombus; and vi) an endovascular system that allows for optional blood perfusion to allow an increase in treatment time.

SUMMARY OF THE INVENTION

The catheter system of the present invention provides novel occlusive material extraction (removal) techniques that utilize sequences of very small electrical discharges between paired electrodes in a fluid-jet arrangement (i) to generate selected fluid flow velocities in a fluid extraction pathway based on Bernoulli's Law of Pressure Differential, (ii) to create selected levels of turbulent fluid flow within a treatment site to remove occlusive material from the vessel walls and suction fluids and entrained embolic particles toward the extraction pathway, and (iii) to emulsify or ablate any embolic particles having a cross-sectional dimension larger than a couple of hundred micrometers.

The novel energy delivery methods associated with the sequenced electrical discharges allow for the design of a catheter working end that has a significantly reduced cross-sectional dimension, when compared to prior art system (cf. FIG. 1A). The catheter system according to invention has about 50% (or less) of the cross-section of the prior art systems described above. Still, the present invention can provide an embolic extraction pathway that has a significantly larger functional cross-section than the prior art system shown in FIG. 1A—as much as 200% to 300% larger.

More in particular, the invention provides an elongate microcatheter sleeve with a distal working end that can be passed through a lumen in tubular anatomic structure to reach a targeted endoluminal site. The catheter sleeve defines an interior passageway surrounded by a catheter wall. The interior passageway may be termed an extraction channel since it is adapted to extract fluid and embolic particles from the endoluminal site. The wall of the catheter sleeve carries small diameter channels (or microchannels) with first and second electrodes for accelerating, or jetting, fluid flows in the proximal direction through an open terminus into the extraction passageway. The electrode carrying channels have a preferred cross-sectional dimension ranging from less than 1 $\mu$m to about 1000 $\mu$m and communicate with a remote fluid media inflow source. The catheter system provides an electrical source coupled to the first and second electrodes together with a computer controller for controlling parameters of electrical discharges between the electrodes, such as the power delivered by an electrical discharge, the profile of energy delivery within a discharge, the length of a discharge and the repetition rate of discharges.

For treating an endoluminal site, for example a partially occluded vascular graft, the physician advances the working end of the catheter to the targeted site. Next, the physician expands the upstream and downstream balloons carried by the working end to occlude the lumen. The endovascular space between the occlusion balloons thus isolates a working space and prevents any embolic particles from migrating downstream. Thereafter, the physician actuates the controller to cause electrical discharges of a sped power and repetition rate within fluid flows in the microchannels thereby causing high velocity flows into the extraction passageway. This aspect of the method of the invention, based on Bernoulli's Law of Pressure Differential, causes a selected level of turbulent fluid flow within the working space as fluids are suctioned toward the extraction passageway. The turbulent fluid flows are used to remove occlusive materials that adhere to the vessel wall. Another aspect of the method of the invention relates to the delivery of mechanical energy in the form acoustic waves to the embolic particles within the fluid extraction pathway that are proximate to the fluid jets. This form of energy delivery, as well as thermal energy delivery, can emulsify, fragment or ablate any embolic particles having a relatively large cross-sectional dimension. The system also can optionally deliver a pharmacological agent (e.g., t-PA) to the working space to further dissolve any particles, which is herein defined as a method of delivering chemical energy to occlusive material within, or remove from, the targeted site.

The fact that the microcatheter comprises a single sleeve member that defines a central extraction passageway distinguishes the invention from the prior art catheter system described above. The microcatheter of the invention only requires two small crosssection fluid carrying lumens in the catheter wall, thus allowing the catheter assembly to have a very small outside diameter. Referring to TABLE B below, one embodiment of catheter sleeve can have an outside diameter of about 1450 μm, which is approximately 50% of the diameter of the prior art outer catheter described in TABLE A above. At the same time, the cross section of the extraction passageway of the present invention can be about 1000 μm, or close to 3 times the diameter of the prior art system (cf. TABLE A). Further, the free working space in the targeted site is larger when using the system of the invention.

TABLE B

| vessel lumen diameter | catheter OD | catheter ID |
|---|---|---|
| 4000 μm or 3000 μm | 1450 μm | 1000 μm |
| WORKING SPACE DIMENSION (min. radial Δ between lumen ID and catheter OD) | EXTRACTION PASSAGEWAY DIMENSION | FLUID INFLOW LUMEN |
| 1275 μm (in 4000 μm lumen) 775 μm (in 3000 μm lumen) | 1000 μm | c. 200 μm |

The small diameter of the working end of the catheter allows it to be used in smaller vessels, as well as to extract and process larger embolic fragments without clogging the extraction passageway. Further, the catheter sleeve of the present invention can be very flexible, in contrast to the prior art systems, to allow the sleeve to access treatment sites in tortuous vessels. Numerous other advantages result from the reduction in diameter of the catheter working end enabled by the present invention.

The catheter system of the present invention advantageously uses electrical discharges to cause high velocity fluid flows to create extraction forces at the catheter working end in accordance with Bernoulli's Law of Pressure Differential to extract fluids and embolic particles.

The catheter system provide fluid flows and fluid turbulence to remove occlusive materials from the vessel walls around a targeted site.

The catheter system advantageously creates high-pressure fluid flows to delivery energy to fluids and entrained particles to emulsify, fragment and ablate embolic particles.

The catheter system advantageously creates cavitation bubbles in fluids in an extraction channel to cause acoustic energy to emulsify occlusive material.

The catheter system provides a fluid media having a selected resistivity for controlling the velocity of fluid flows by altering the effect of an electrical discharge.

The catheter system of the invention provides extraction forces within a working space isolated by first and second occlusion balloons to prevent embolic particles from migrating downstream.

The catheter system advantageously creates a selected high pressure differential by expanding the volume of a fluid media in a confining channel in a phase state change.

The catheter system creates a high pressure jetting effect to create selected fluid velocities in a preferred range of about 1 m/s to about 10 m/s.

The catheter system advantageously utilizes an electrical energy source for delivering electrical discharges to the working end that is reliable and inexpensive.

BRIEF DESCRIPTION OF THE DRAWINGS

Other objects and advantages of the present invention will be understood by reference to the following detailed description of the invention when considered in combination with the accompanying Figures, in which like reference numerals throughout are used to identify like components throughout this disclosure.

FIG. 2 being perspective view of the hypothetical tubular member with side openings and an open end; FIG. 3 being a sectional representation fluid flows within the hypothetical tubular member of FIG. 2.

FIG. 14A being a view of the inflow of fluid media into an endovascular working space isolated between deployed upstream and downstream occlusion balloons;

FIG. 14B being a view of the fluid flows and turbulence within the endovascular working space that removes occlusive material from the vessel walls caused by pulsed electrical discharges of FIG. 14C; and FIG. 14C being an enlarged graphic view of pulsed electrical discharges that create high-velocity fluid flows into the extraction passageway (i) to create a pressure differential between the extraction passageway and the working space to transport fluids into and though the extraction passageway, (ii) to cause turbulent flows in the endovascular workspace to remove occlusive material from vessel walls, and (iii) to deliver energy to fluids and entrained occlusive materials during transport of such materials to fragment, emulsify or ablate such occlusive materials.

DETAILED DESCRIPTION OF PREFERRED SYSTEM EMBODIMENTS

I. Principles Relating to Extraction and Emulsification of Emboli Based on Pressure Differential Daniel Bernoulli, an eighteenth-century Swiss scientist, discovered that as the velocity of a fluid in cases, its pressure decreases—often called Bernoulli's Law. The catheter system according to the present invention utilizes a microelectrical discharge system for providing high repetition rate discharges in small channels (herein termed a microchannel structure) in a catheter working end to create high velocity fluid flows as a novel means of exploiting Bernoulli's Law for medical therapeutic purposes. The high velocity fluid flows created by the invention, together with selected levels of turbulence generated by such fluid flows, are adapted for use in catheter based medical interventions in a very small endoluminal working spaces. More in particular, the invention utilizes a sequence of electrical discharges for the purposes of: (i) creating a pressure differential to draw a fluid through a working space in a lumen (e.g., a graft or native blood vessel) with a sufficient turbulence to cleanse the working space and to entrain emboli in a fluid flow; (ii) emulsifying or ablating the larger embolic fragments as they enter an extraction pathway in the catheter, and (iii) creating a pressure differentials within the entire length of an elongate extraction channel to carry the embolic fragments through the catheter to a proximal handle for collection.

Figure 1A:
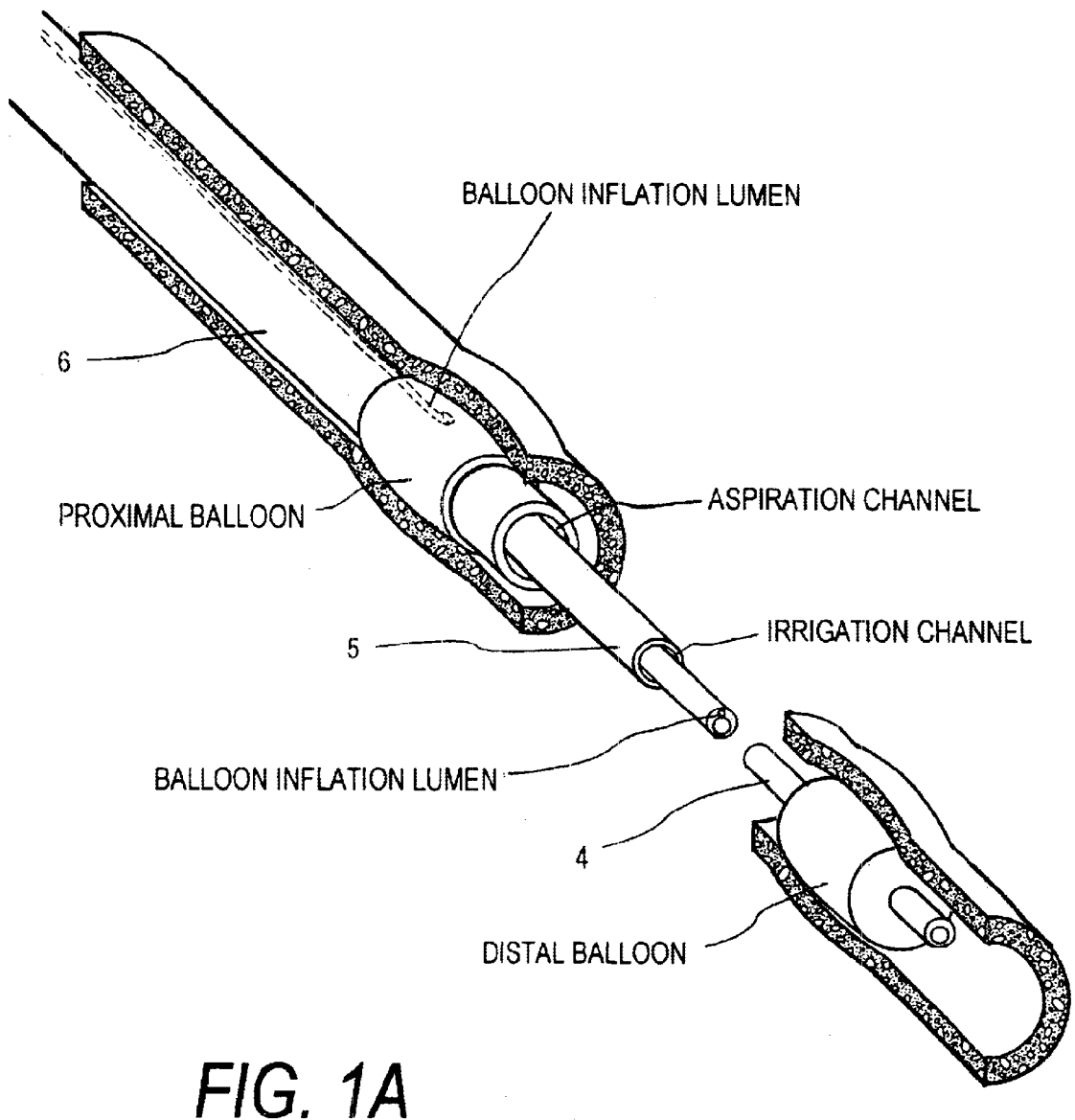
FIG. 1A is a perspective cut-away view of a prior art catheter working end
Figure 1B:
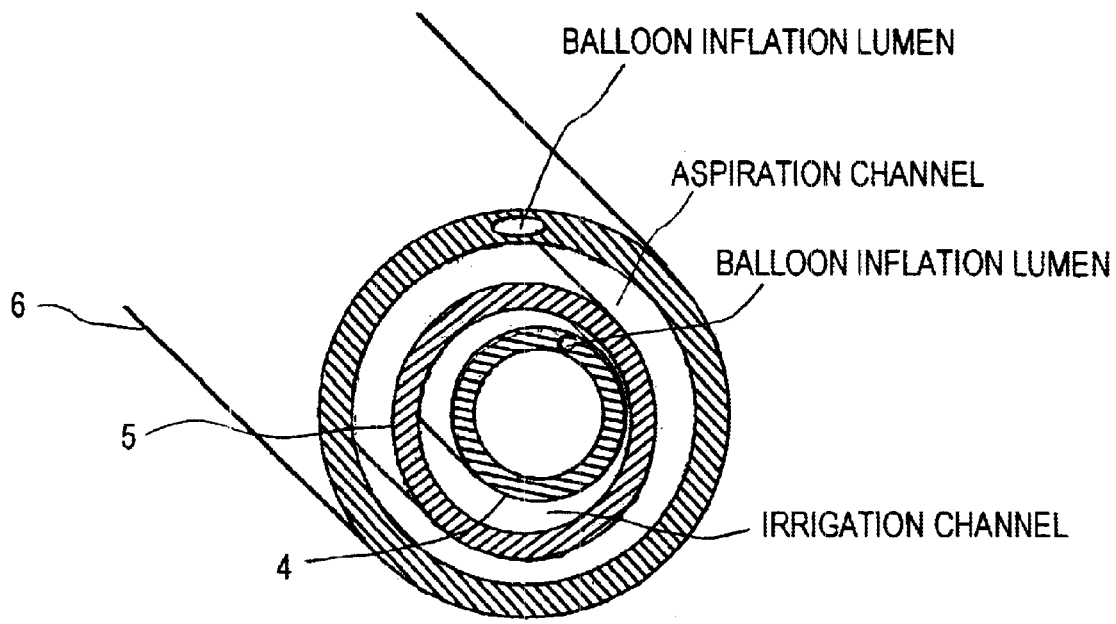
FIG. 1B is a cross-sectional view of the prior art catheter working end of FIG. 1A.
Figure 2:
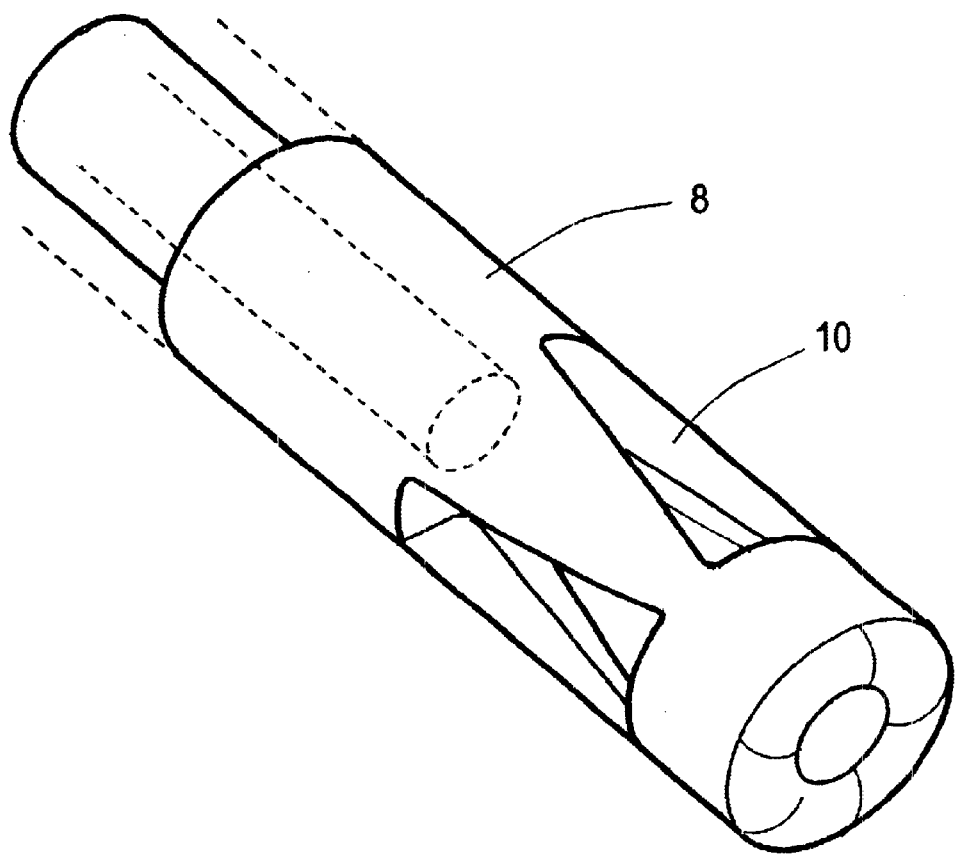
FIGS. 2–3 are view of a hypothetical tubular member that explains Bernoulli's Law as it applies to the principles of the invention.
Figure 3:
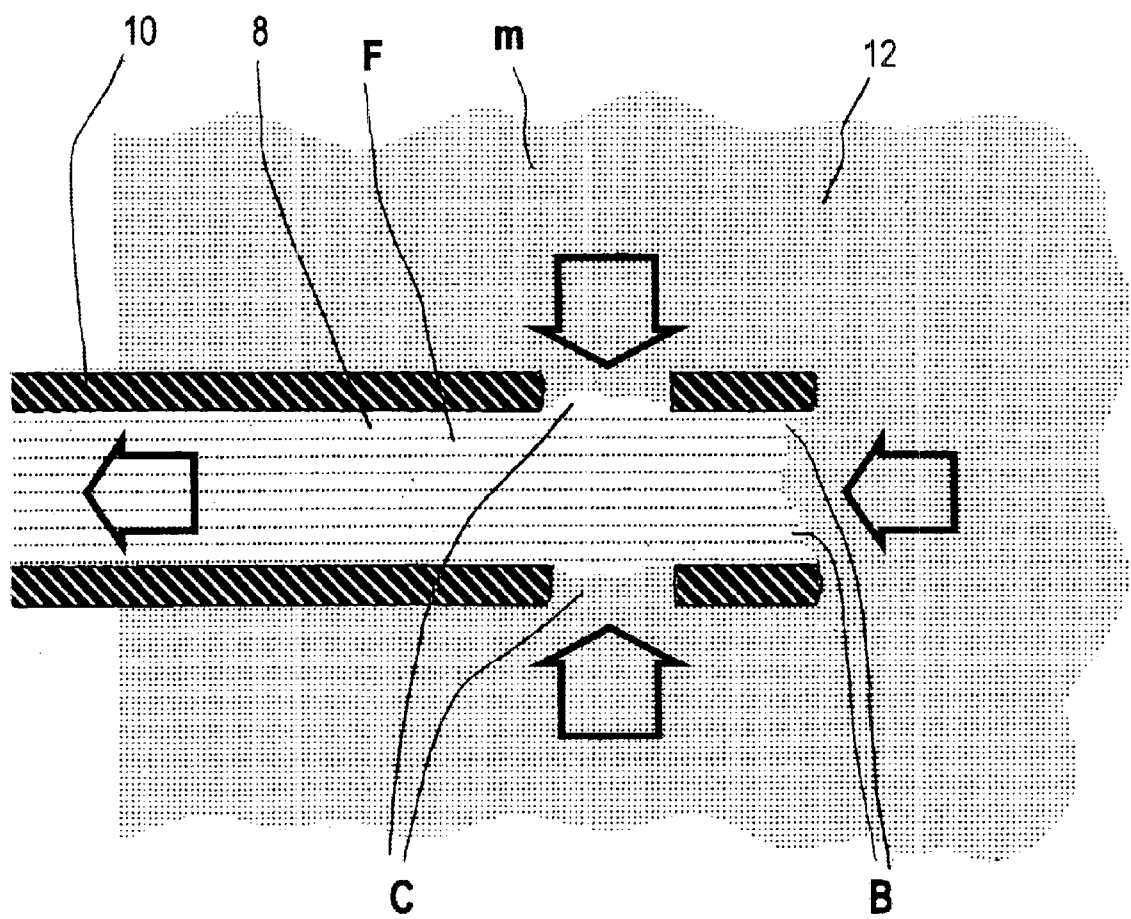

FIGS. 2 and 3 are schematic view of a simple tubular member or working end that defines the principles of the invention. By understanding the schematic arrangement of FIGS. 2 and 3, it is possible to understand how the invention exploits such principles in the construction of a functional catheter working end The arrangement of FIG. 3 assumes that a fluid or media m is caused to move at a selected velocity in a flow indicated at F. The flow can be generated by hypothetical means at location B such that the fluid media m then flows at a high velocity in interior pathway 8 bounded by region C within the tubular member 10. In region C, energy is used as the molecules of the fluid media accelerate which leaves less energy to exert pressure laterally, and such pressure thus decreases at the boundary of the media flow F. One way to describe this decrease in pressure is to call it a differential pressure, as will be used herein. This means that the low pressure region at the boundary of the media flow F is different from the pressure at any other location in the surrounding fluid media m, whether the media is a gas or a liquid. In other words, the fluid pressures are higher in regions indicated at 12 than at the boundary of the fluid flow F. For this reason, the underlying principle is often called Bernoulli's law of Pressure Differential.

The lower pressure at the boundary of the flow F produces suction forces that can pull in fluid volume, and entrain particles, from the surrounding fluid environment as indicated by the arrows in FIG. 3. For example, in a venturi structure that is somewhat analogous to the present invention, an incompressible, inviscid fluid moving into a region having a different cross-sectional area (A) undergoes a change in velocity (v). The product A·v remains constant. $P_1 A_1 v_1 = P_2 A_2 v_2$. If the fluid is incompressible, $P_1 = P_2$ and they cancel to give: $A_1 v_1 = A_2 v_2$ (an equation of continuity). For the velocity to undergo change, there must be a change in force. A change in force results in a change in pressure. Thus, the (lateral) pressure exerted by an incompressible fluid varies inversely with the square of the speed of the fluid, which equation is Bernoulli's law or principle. As will be described below, the present invention utilizes sequenced electrical discharges within a series of small bores (channels or microchannels) to cause a high velocity fluid jetting effects in the central extraction channel of a catheter which, in turn, creates the desired pressure differentials within, and about, the working end of the catheter of the present invention.

Figure 4:
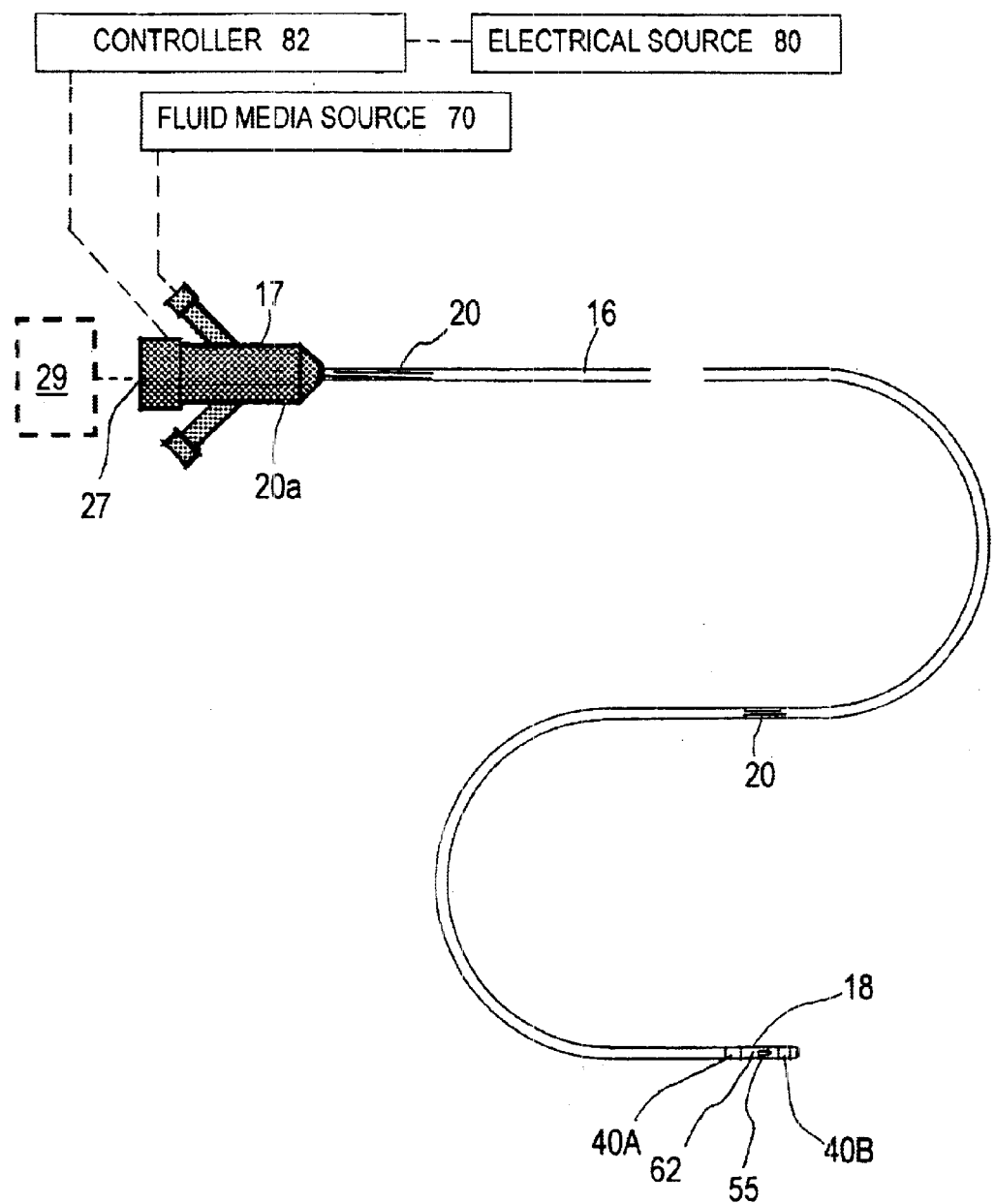
FIG. 4 is a plan of a Type "A" catheter system with a block diagram of the electrical source, controller, and fluid media source of the invention.
Figure 5:
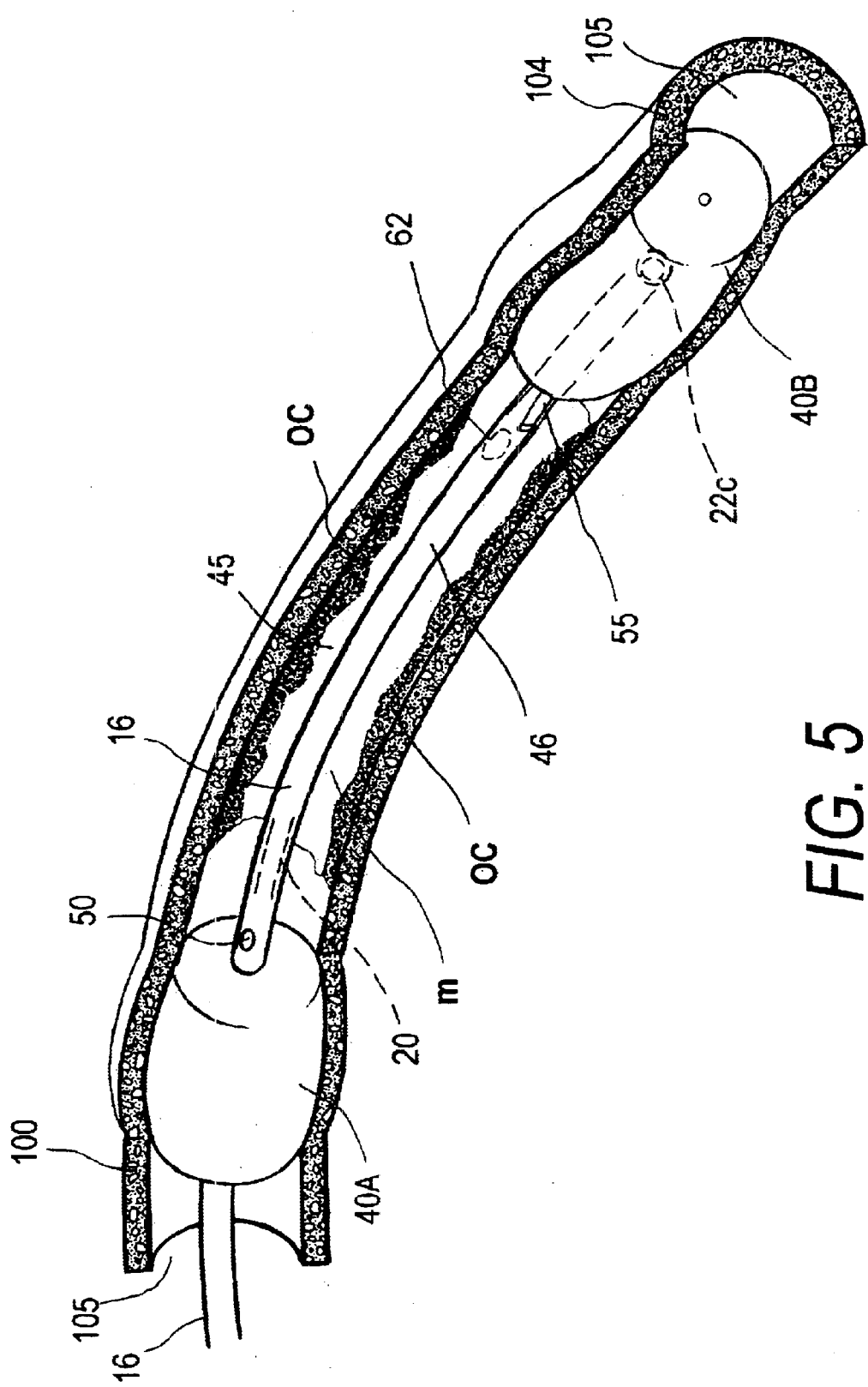
FIG. 5 is a perspective view of the Type "A" catheter working end deployed in a targeted endovascular site with the dual occlusion balloons in an expanded state.
Figure 6:
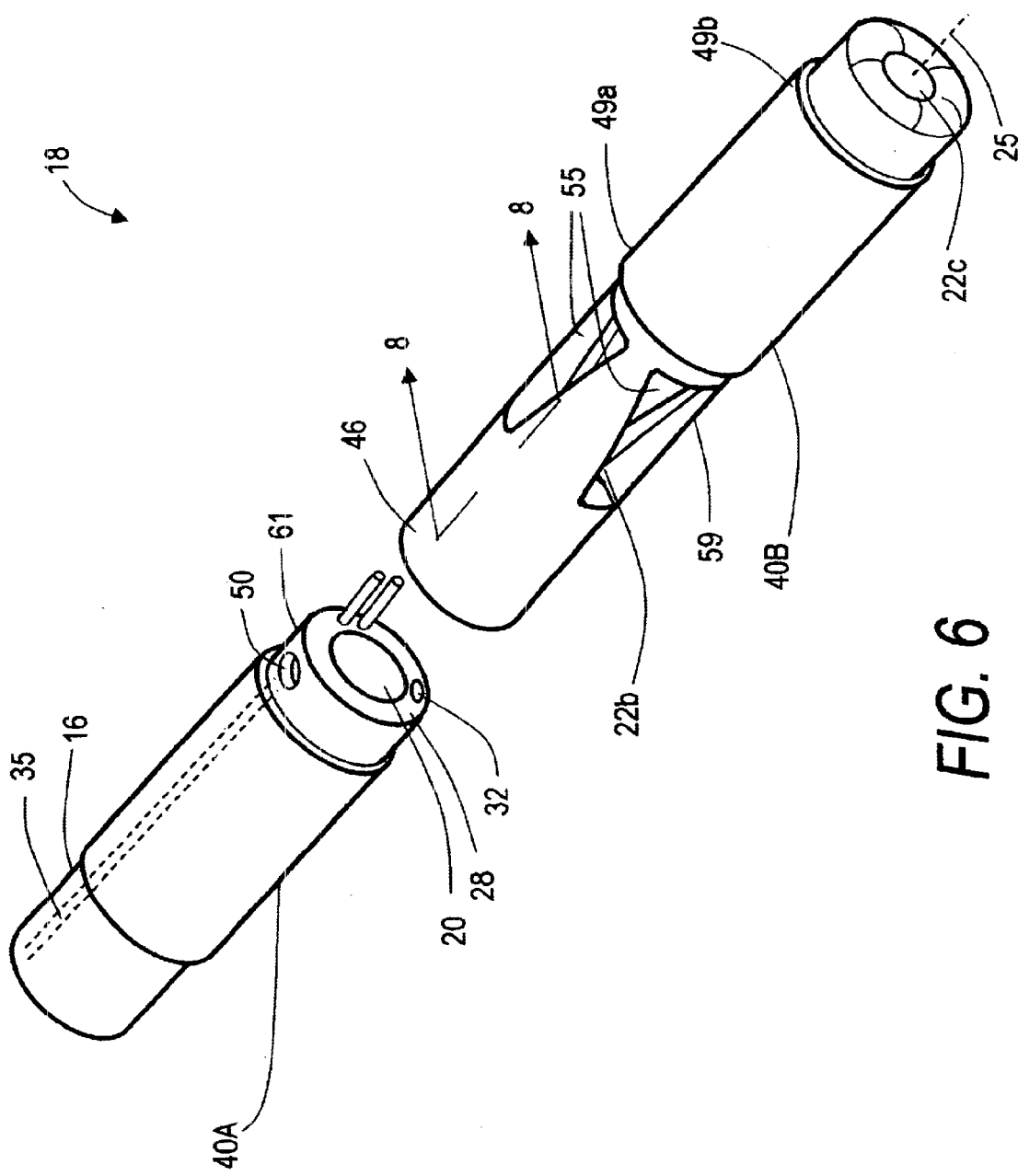
FIG. 6 is an enlarged cut-away view of the working end of FIG. 5 showing the dual occlusion balloons in a pre-deployed (collapsed) state.

II Construction of Exemplary Type "A" Endovascular Intervention System for Removal of Embolic Particles Referring to FIG. 4, a Type "A" catheter system 15 corresponding to the invention is shown having a thin-wall catheter sleeve member 16 that extends from a proximal handle or manifold 17 to distal working end 18. FIGS. 5 & 6 show that the flexible catheter sleeve 16 has a bore or internal pathway 20 extending through the length of the sleeve along longitudinal axis 25. The internal channel or pathway has a proximal portion 22a extending to the catheter handle, a medial portion 22b within the working end 18 and an open distal terminus 22c. This pathway may also be termed herein an extraction channel for extracting fluids and embolic materials from a treatment site. The catheter sleeve 16 is extruded of a flexible material, such as, high density polyethylene, PTFE, polyolefin, Hytrel® or another suitable material known in the art of catheter fabrication, with or without a braid reinforcement. The internal passageway 20 of catheter sleeve 16 extends proximally to an open proximal end 27 in manifold 17 as is common in catheter construction. A collection reservoir 29 of any suitable type communicates with the open proximal end 27 of the passageway for collecting extracted fluid and embolic fragments. In this exemplary embodiment, the outer diameter (OD) of catheter sleeve 16 may range from about 1.0 mm. to about 3.0 mm, but larger diameter catheters also fall within the scope of the invention for treating larger vessels. The internal passageway 20 of the catheter sleeve has any suitable inner diameter (ID) that cooperates with the selected outer diameter, and the interior channel is adapted have multiple functionality, namely comprising a bore for a guidewire 30 (see FIGS. 5 & 6) before being used as an emboli extraction pathway. The wall 28 of catheter sleeve 16 can be of any suitable thickness sufficient to generally prevent the channel 20 from collapsing as the sleeve flexes and for carrying first and second small diameter inflow lumens indicated at 32 and 35, which will be further described below. In one embodiment, the internal passageway 20 can ranges between about 750 µm and 1000 µm, with flattened inflows lumens 32 and 35 resulting in an outside catheter diameter of 1500 µm. An exemplary catheter for treating a CABG patient can have an overall length of about 120–150 cm. for introduction from the patient's groin, or any shorter length of instrument sleeve (whether rigid or flexible) for other endoluminal treatments.

Referring to FIGS. 5 & 6, the working end 18 carries an occlusion balloon system that comprises first proximal balloon member 40A and second distal balloon member 40B that have a first collapsed position (FIG. 6) and a second expanded or inflated position (FIG. 5) for engaging the walls of a vessel. Each balloon member 40A and 40B has a respective internal inflation chamber 44a and 44b that communicates with inflow lumen 32 within the catheter wall 28 for inflating the balloons with a fluid (e.g., any suitable liquid or gas). The region between the occlusion balloons defines a treatment area or working space 45 around the catheter sleeve (see FIG. 5). The catheter surface portion indicated at 46 between the balloons will, in alternative embodiments, be provided with additional treatment system components such as stent deployment means. However, the basic embodiment of FIGS. 5 & 6 (without additional treatment components) can be used independently to treat occluded vascular grafts by turbulent flows of a fluid media m to remove occlusive material oc as will be described further below in the method of the invention.

Figure 7A:
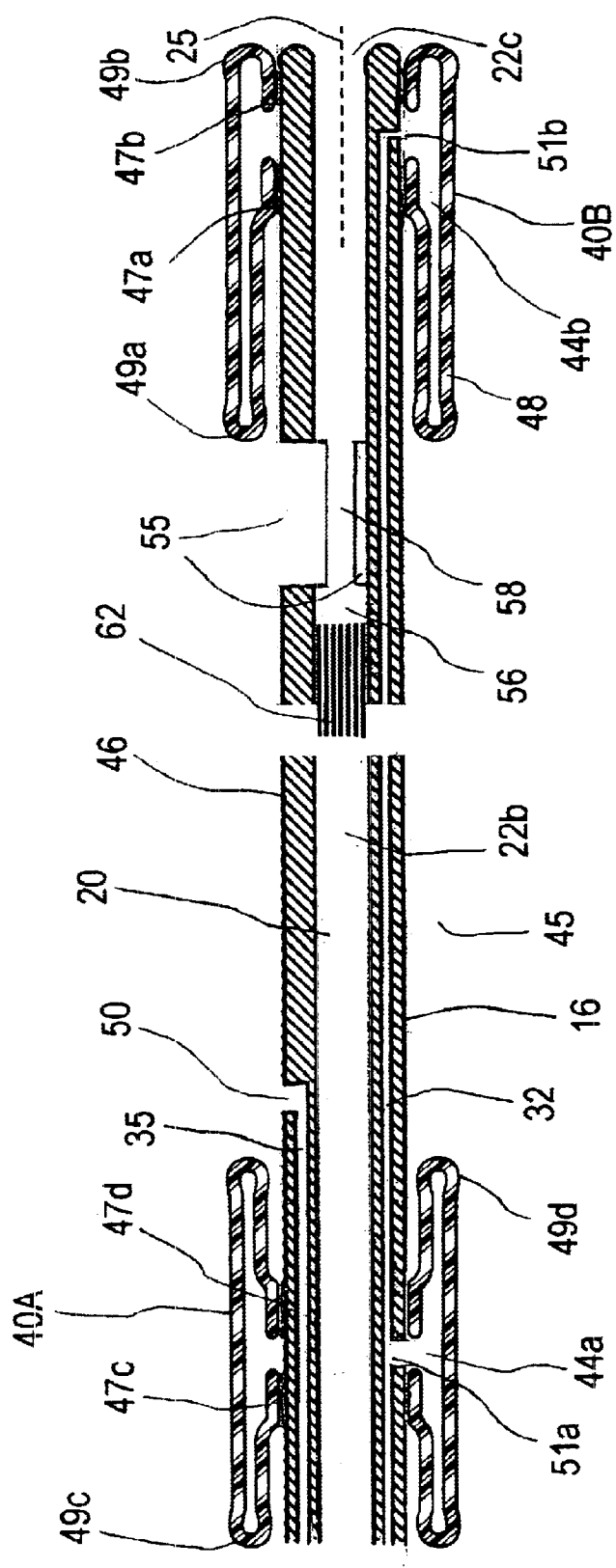
FIG. 7A is a sectional view of the working end of FIG. 6 taken along line 7A—7A of FIG. 6 showing the manner in which the occlusion balloons are attached to the catheter sleeve.
Figure 7B:
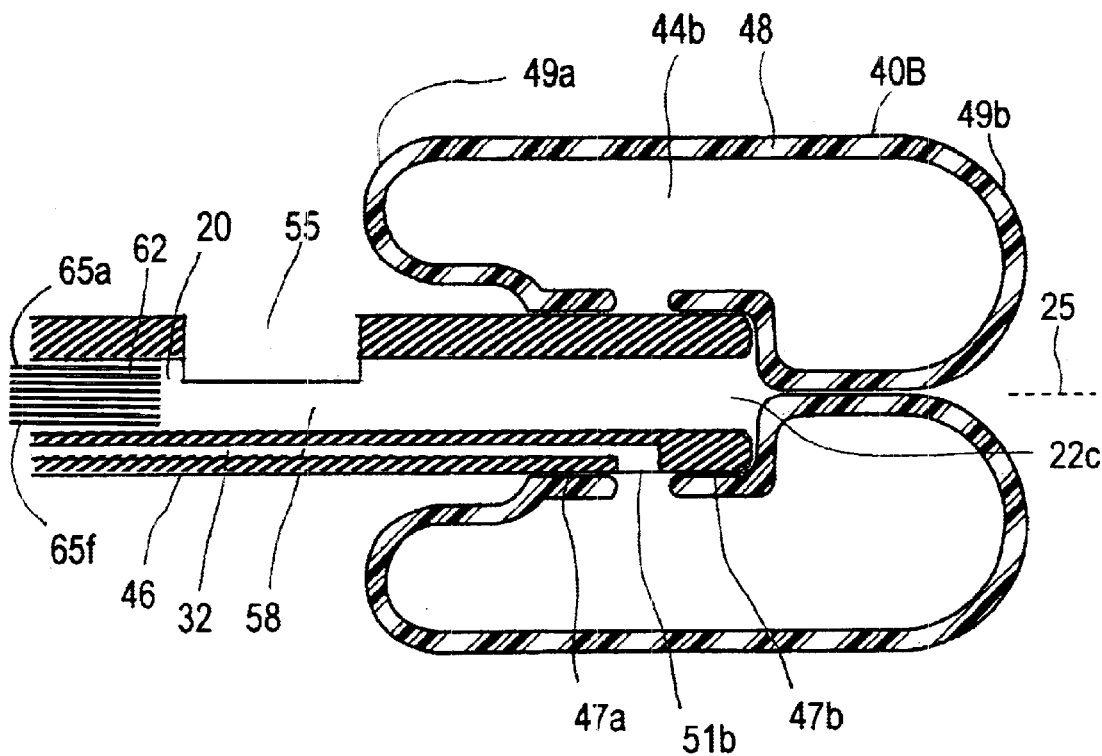
FIG. 7B is a sectional view of the distal balloon of FIG. 5 taken along line 7B—7B of FIG. 5 showing the distal balloon in a deployed state with a balloon wall adapted to roll distally.

The occlusion balloon system of this exemplary embodiment has several novel features. Since the balloon system is not a high-pere system, for example as used in stent expansion, the dual balloons are supplied with an inflation medium from a single source through a single inflation lumen 32. This aspect of the invention allows for more rapid balloon deployment and also equalizes the pressure within inflation chambers 44a and 44b of the balloons since they remain coupled to the same inflation lumen. The use of a single inflation lumen thus allows for a smaller cross section of the catheter sleeve 16. The balloons may be made of any suitable compliant or non-compliant material known in the art, and preferably are of a material such a form of latex, silicone, irradiated polyethylene or a proprietary material such as C-Flex®. FIGS. 7A–7B show another novel feature of the balloon system which relates to the manner in which the distal balloon 40B is attached to catheter sleeve 16, or optionally the manner in which both balloons are attached to the catheter sleeve. FIG. 7A shows a schematic sectional view of second distal balloon 40B in a collapsed position with proximal seal portion 47a and distal seal portion 47b that attach the balloon to sleeve 16. The distal balloon 40B is formed in a shape so that the balloon wall 48 defines rolling proximal and distal end portions 49a and 49b that can over-roll the seal portions 47a and 47b. In this regard, referring to FIG. 7B, the second (distal) balloon 40B is shown in its second expanded position wherein its distal end portion 49b has over-rolled the open terminus 22c of bore 20 in catheter sleeve 16 to thus substantially seal the end of the extraction channel as the balloon walls are pressed together about the centerline or axis 25 of the catheter sleeve. This aspect of the invention allows the axial bore 20 within catheter sleeve 16 to initially have an open terminus to pass over a guidewire 30, and then later to be sealed at its distal terminus 22c to use the same bore 20 for emboli extraction. Further, it can be appreciated that this feature incorporated into at least one of the paired occlusion balloons will allow the two balloons to be inflated simultaneously without the risk that each balloon would prematurely grip the vessel wall and then stretch the axial length of engaged vessel as the balloons are further inflated. Rather, the proximal balloon 40A can inflate and grip the vessel wall and the distal balloon 40B will then over-roll its attachment points (seal portions 47a and 47b) to self-regulate the length of treatment area 45 as well as to block the distal terminus 22c of the catheter bore 20. (It should be appreciated that the proximal balloon 40A optionally can be sealed to sleeve 16 to provide the over-rolling feature with similar seal portions 47c and 47d to allow its ends 49c and 49d to roll over the attachment points as shown in FIG. 7A). A final feature of the occlusion balloon system is shown in FIG. 7A wherein the lumen portion or port 51a between the common inflation lumen 32 and proximal balloon chamber 44a is substantially larger than lumen portion or port 51b between the common inflation lumen 32 and distal balloon chamber 44b. This allows the proximal balloon 40A to be inflated slightly more rapidly to fully engage the vessel walls while the distal balloon deployment time lags slightly when both are inflated from the common inflation lumen 32, thus facilitating the distal rolling of the wall 48 of balloon 40B over the distal end of the catheter as shown in FIG. 7B.

Figure 8:
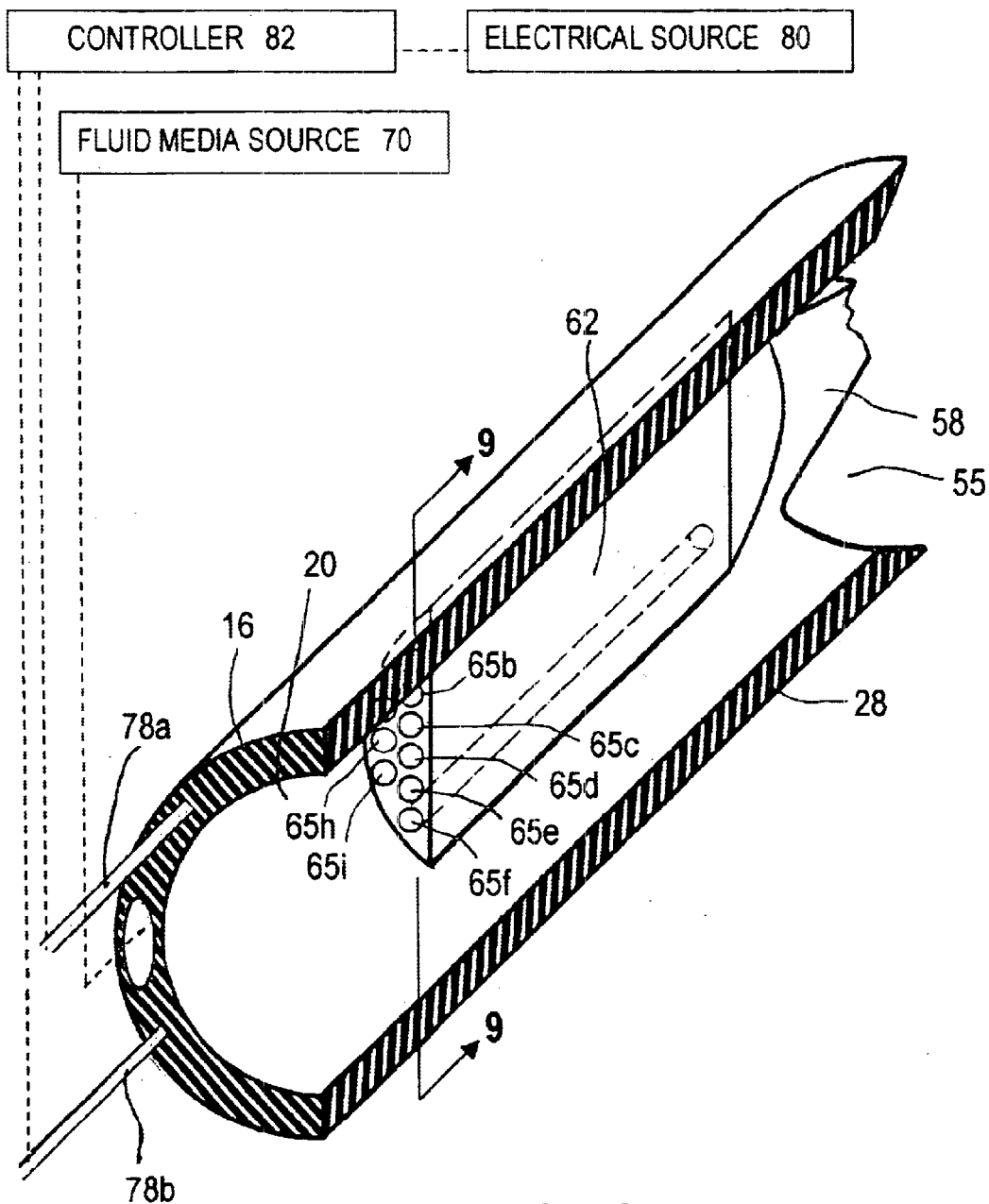
FIG. 8 is an enlarged perspective cut-away view the structure of electrode carrying channels of the working end of FIGS. 5 & 6 taken along line 8—8 of FIG. 6.

FIG. 8 shows an enlarged cut-away view of a portion of working end 18 to explain the micro-electrical discharge system corresponding to the present invention for creating high-velocity fluid flows. Referring back to FIG. 6, the catheter surface indicated at 46 between the balloons, also called herein a working surface, has a series of openings or ports 55 (collectively) in the wall 28 of the catheter sleeve 16 that provide fluid communication between the working space 45 in a targeted vessel with an interior chamber portion 56 (also called pressure differential chamber) of extraction pathway or bore 20. The longitudinal web elements 58 between the ports 55 are wide enough to offer structural strength to catheter sleeve 16, but otherwise the ports 55 are as large as possible to allow fluid flow and pressure differentials (resulting in suction forces) to freely communicate between chamber 56 of bore 20 and the working space 45 in the targeted site of a vessel. Otherwise, the ports 55 and webs 58 may range in number from 2 to about 6 and 12 and fall within the scope of the invention. The exemplary embodiment of FIGS. 6 & 8 shows three ports that define a similar number of longitudinal webs 58 therebetween. In this embodiment, one of the webs 58 also is adapted to carry lumen 32 (not shown) that extends through the catheter wall to inflation chamber 44b of distal balloon 40B.

In this embodiment, as will be described below, it is preferable to locate ports 55 in the distal region 59 of working surface 46. As can be seen in FIGS. 5 & 6, a fluid inflow port 50 is located in proximal region 61 of working surface 46 and is adapted to cooperate with ports 55 by thereby providing a fluid flow that will circulate from the proximal end of working space 45 to the distal end thereof. The fluid inflow port 50 communicates with inflow lumen in the wall of the catheter sleeve and is adapted to deliver a selected fluid media m such as saline solution to the working space 45.

Now turning to FIG. 8, a portion of wall 28 of catheter sleeve 16 in close proximity to ports 55 carries the electrical discharge component, or microchannel body structure 62 of the invention (i) for initiating turbulent circulation of media m through working space 45 to cleanse occlusive material oc from the vessel wall, (ii) for accelerating fluid flows in extraction pathway 20 to suction fragments of occlusive material into pathway 20, and (iii) for emulsifying embolic fragments drawn into pathway 20 as the fluid media m entraining the emboli are moved toward the catheter manifold FIG. 8 shows that plurality of small diameter channels or bores 65a–65i with first and second ends in an insulated body portion 66 that is formed into, or coupled to, the wall 28 of catheter sleeve 16. In this embodiment, the channels 65a–65i are formed in a suitable insulative material that is then bonded to the interior of catheter sleeve 16. The number of channels may number from a singular channel in a very small diameter extraction lumen 20 to 100's of microchannels if the channels are micronized or if the extraction channel 20 is substantially large as will be discussed below.

Still referring to FIG. 8, each channel 65a–65i has a first (distal) end 68 (collectively) that communicates with the terminus 69 of fluid inflow lumen 35 that is provided in wall 28 of the catheter sleeve to carry fluid media m to the working space 45 and channels 65a–65i from a remote fluid source 70. Each channel 65a–65i has a second terminal end 72a–72i that faces in the proximal direction within' or toward, the axial bore or pathway 20 in the catheter sleeve. The method of the invention, in part, utilizes electrical discharges in channels 65a–65i to create high velocity fluid flows (or jets) of fluid media m to exit the open terminal ends 72a–72i of the channels into bore 20 to thereby induce a pressure differential between the extraction lumen 20 and the fluid media m within working space 45 of the vessel.

Figure 9:
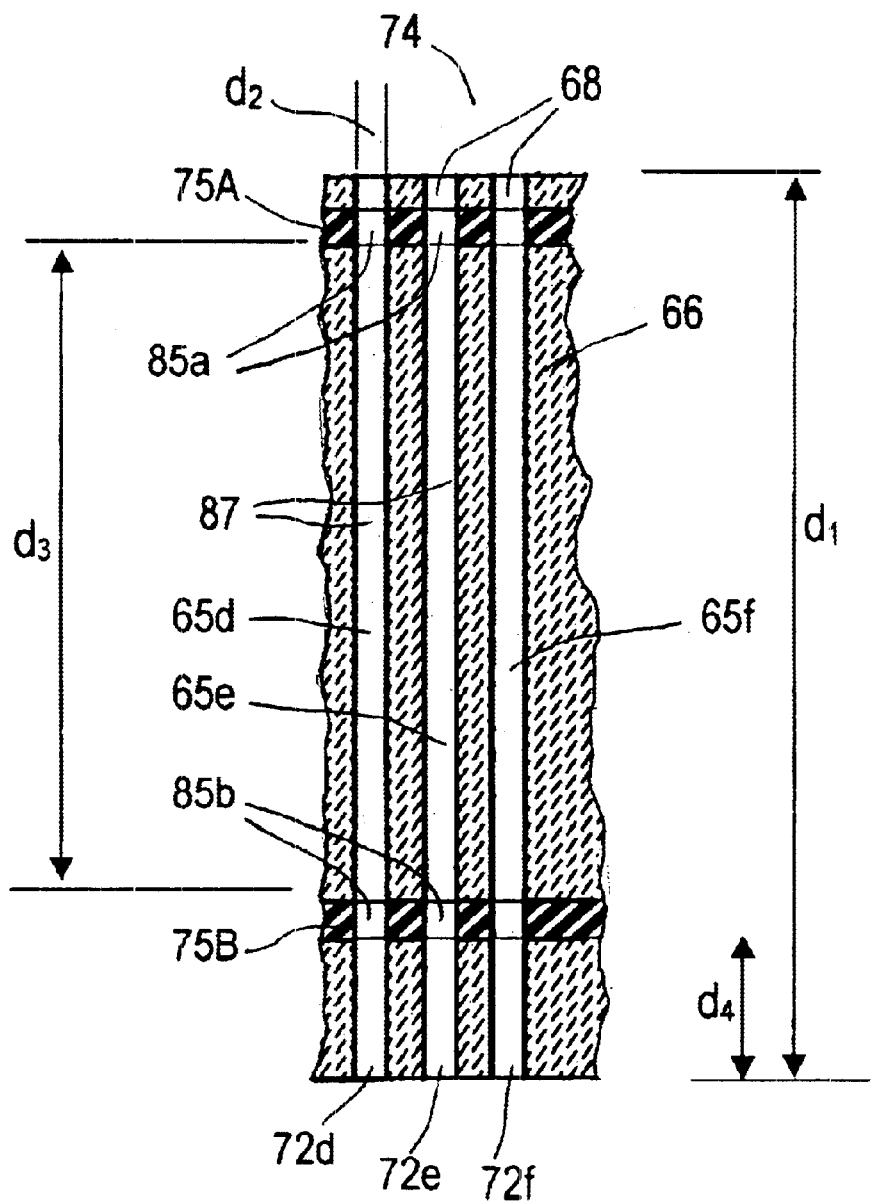
FIG. 9 is a greatly enlarged longitudinal sectional view of several microchannels showing an exemplary electrode configuration taken along line 9—9 of FIG. 8.

Referring now to FIGS. 8 & 9, the exemplary microchannel body structure 62 and its method of use will be described in more detail. In this embodiment, the channels 65a–65i are substantially aligned with axis 25 of the catheter bore 20. In FIG. 8, it can be seen that an insulative body material 66 carries the channels 65a–65i. The body 66 is molded or machined of a suitable plastic or other non-conductive material that includes a form or chamber portion 74 for distributing the fluid media m to the distal ends 68 of channels 65a–65i. Thus, it can be seen that fluid media m can flow from remote pressurized fluid source 70 through inflow lumen 35 to chamber portion 74 and thereafter through each microchannel to exit open ends 72a–72i thereof. As will be described below, the single inflow lumen 35 is thus adapted to provide an inflow of fluid medium m to the working space 45 in a selected flow rate determined by (i) a pressure mechanism applied to media m from fluid source 70; (ii) the dimensions of port 50 that communicates with working space 45, and (iii) the cooperating rate of flow (i.e., taking into consideration backflow resistance) through the same lumen to the microchannel body 62 via chamber portion 74 and channels 65a–65i. It should be appreciated that separate inflow lumens may be provided for carrying fluid to working space 45 and microchannel body 62. The axial length $d_1$ of the channels 65a–65i is between about 0.5 mm. for very small diameter instruments to about 10.0 mm. for very large diameter instruments (see FIG. 9). More preferably, the axial length $d_1$ of the channels is between about 2.0 mm. and 5.0 mm.

Certain scales of channels 65a–65i can be fabricated by conventional machining or molding processes to make any form of channel with a relatively large diameter. For fabrication of a scaled-down microchannel structure 62, the fabrication can be accomplished by plasma-type semiconductor processing as in known in the art of silicon chip manufacturing and the MEMS field (microelectrical machining). In the case of semiconductor processing methods, the insulator material of a microchannel structure may be silicon or any other suitable insulative substrate. Alternatively, the process can be the same as used to make commercial microchannel plates (MCP). A commercial MCP is a device that is fabricated for photodetection purposes. In an MCP, a tubular cladding glass is mechanically supported in its bore by the insertion of a rod of etchable core glass to produce a potential microchannel. The assembly is then pulled through an oven and drawn down in diameter to produce a microchannel (when the core is etched away). A plurality of such drawn assemblies then are stacked and drawn down through the oven repeatedly until a selected diameter is achieved for the core. Thereafter, the assembly is fused together and the cores are etched away leaving the microchannel. While commercially available MCP's typically may have channels or capillaries ranging from about 5 μm and 25 μm in diameter for photodetection purposes, it can be seen that any suitable diameter of channels can be fabricated by the above methods.

As illustrated in FIGS. 8 & 9, the channel body 62 has electrodes 75A and 75B fabricated in any suitable manner to provide spaced apart electrode surfaces in each channel 65a–65i. In one manner of fabricating a very small diameter channel structure 62 for research, the structure and the electrode layers can be assembled from two commercially available MCP's, with the plates sandwiched together (i) after depositing an electrically conductive layer on the separate plates as is known in the art to serve as the electrodes layers 75A and 75B, and (ii) then substantially aligning and assembling the two microchannel plates. If the microchannel structure is fabricated by conventional semiconductor processing methods, such processes can create both the microchannels in an insulator material and the electrode layers electrodes 75A and 75B.

Referring to FIG. 9, the diameter $d_2$ of each channel may range between about 1 μm and 1000 μm, for small diameter and large diameter instruments, respectively. More preferably, diameter $d_2$ of the microchannels 65a–65i ranges between about 5 μm and 500 μm. The number of channels in body portion 62 relates to channel diameter as well as the diameter of the working end. It should be appreciated that the catheter working end 18 may greatly reduced in scale, and therefore the scope of the invention includes any number of channels in a working end, including a single channel in a side wall of the working end As can be seen FIGS. 8 & 9, electrical leads 78a and 78b of opposing polarity extend from electrical source 80 and are connected to the respective first and second electrode layers 75A and 75B, wherein the more distal electrode is indicated at 75A, and the more proximal electrode indicated at 75B. A computer controller 82 interfaces with electrical source 80 to control all operational parameters of electrical energy delivery. The controller 82 can be programmed to generate trains of electrical energy discharges between electrodes 75A and 75B at a selected repetition rate, or at modulated repetition rate in response to feedback from sensors in the system that sense selected operational parameters. For example, sensing circuitry may be provided to determine a selected impedance range across electrodes 75A and 75B that indicates fluid media within the channel, or a thermocouple can be provided near the open ends of channels 65a–65i to terminate or modulate energy delivery at a selected temperature level.

Figure 10:
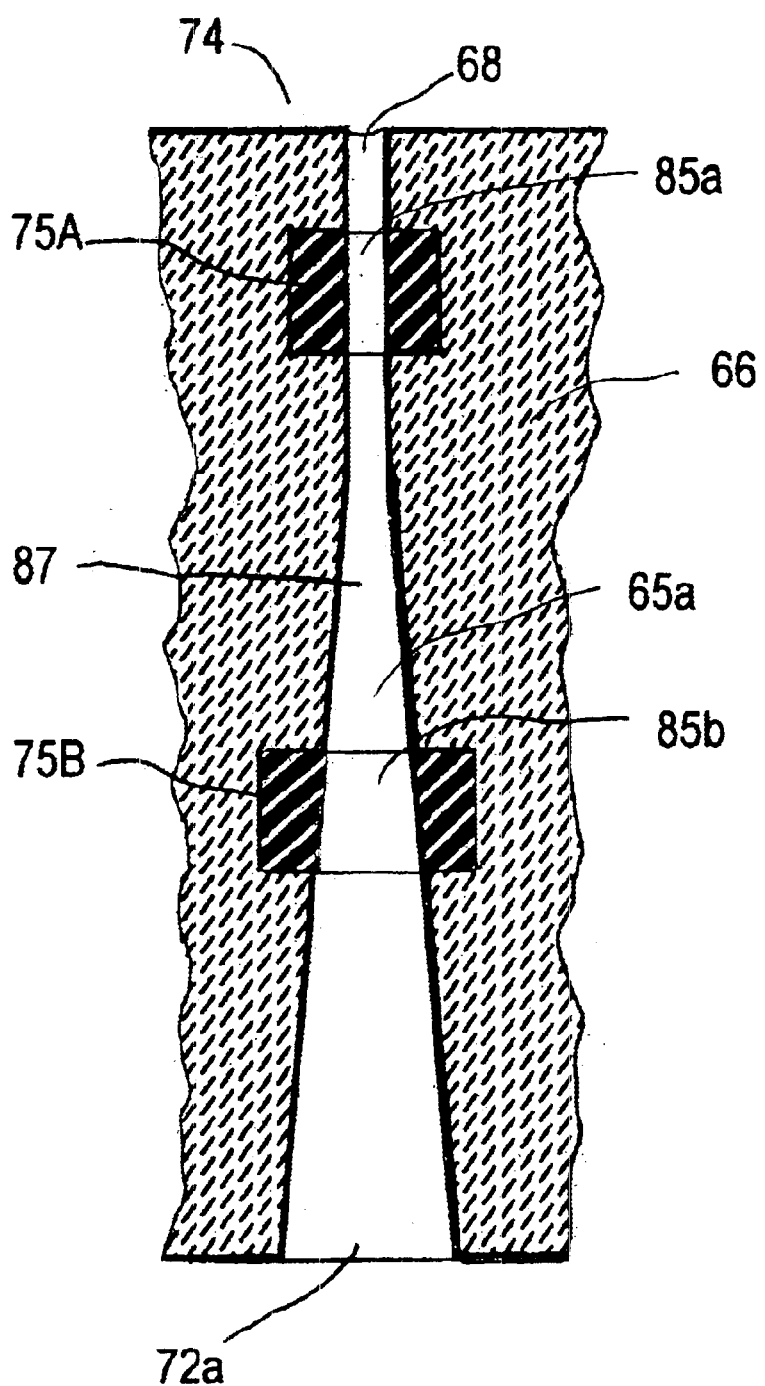
FIG. 10 is a sectional view of alternative embodiment of a single microchannel with a tapered shape together with first and second electrodes.
Figure 11:
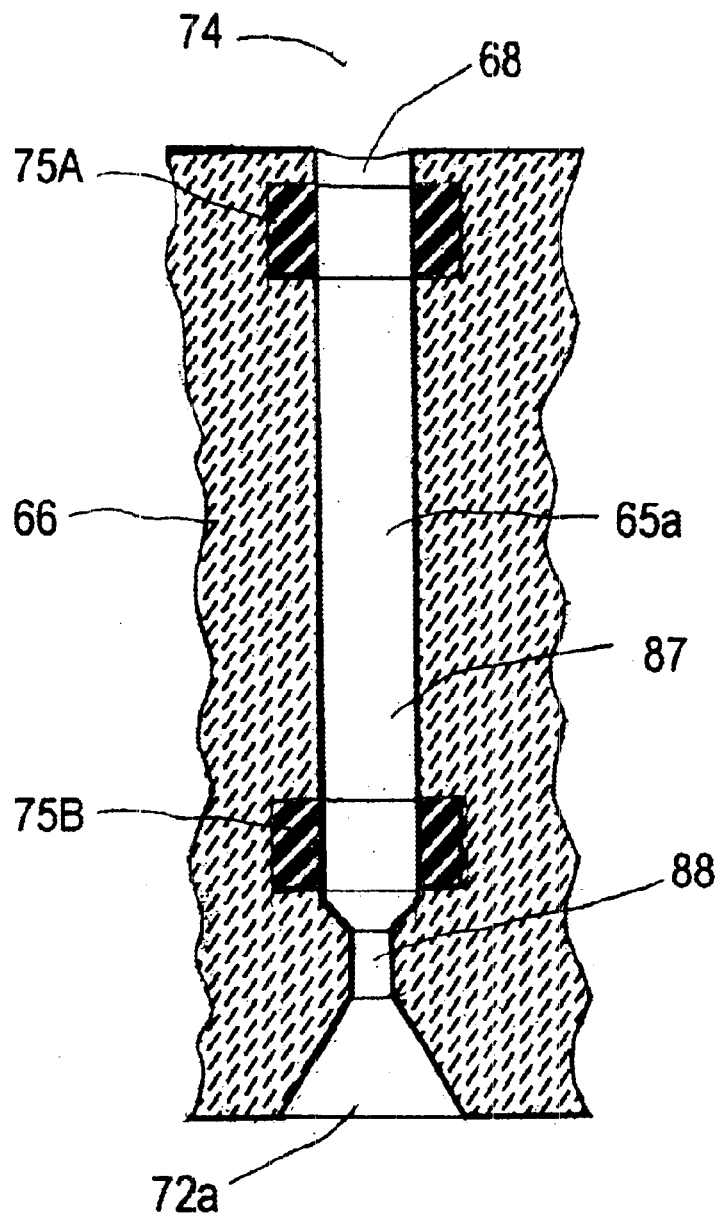
FIG. 11 is a view of alternative embodiment of a microchannel with a venturi and first and second electrodes.

Referring to the not-to-scale sectional view of FIG. 9, the paired electrode layers 75A and 75B have exposed surfaces 85a and 85b within the channels, respectively. These electrode surfaces 85a and 85b are spaced apart by dimension $d_3$ that ranges from about 10 μm to about 5.0 mm. The proximal electrode 75B is spaced apart from the open channel terminations 72a–72i by a suitable length dimension $d_4$ ranging from about 0 μm to 2000 μm so that a layer of insulative material 66 is provided over the electrode. While FIG. 9 shows that the medial channel portion 87 between the electrodes 75A and 75B, as well as the terminal channel portion between electrode 75B and open channel terminations 72a–72i comprise a straight bore, it is preferable in larger channels to provide an increasing bore diameter in medial channel portion 87 in the proximal direction as shown in FIG. 10. Another preferred shape, if the scale of the channels permits, is to provide a venturi shape 88 generally proximate to electrode 75B to further enhance the velocity of fluid as it exits the open channel terminations 72a–72i into extraction channel 20 (see FIG. 11).

Figure 12:
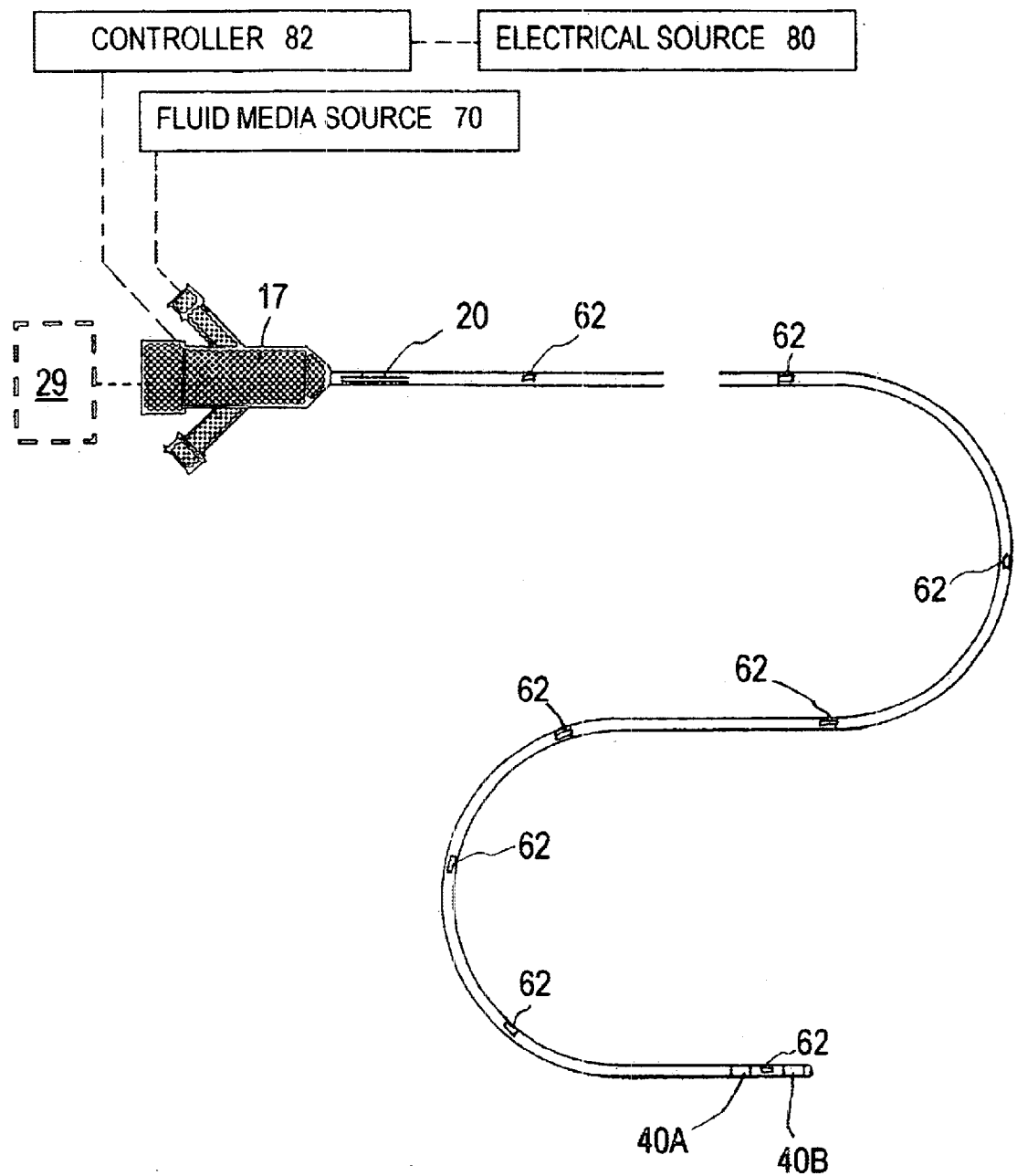
FIG. 12 is a plan view of alternative embodiment of catheter sleeve that carries a series of microchannel structures along the entire length of the catheter sleeve for accelerating fluid flows along the length of the sleeve.
Figure 13:
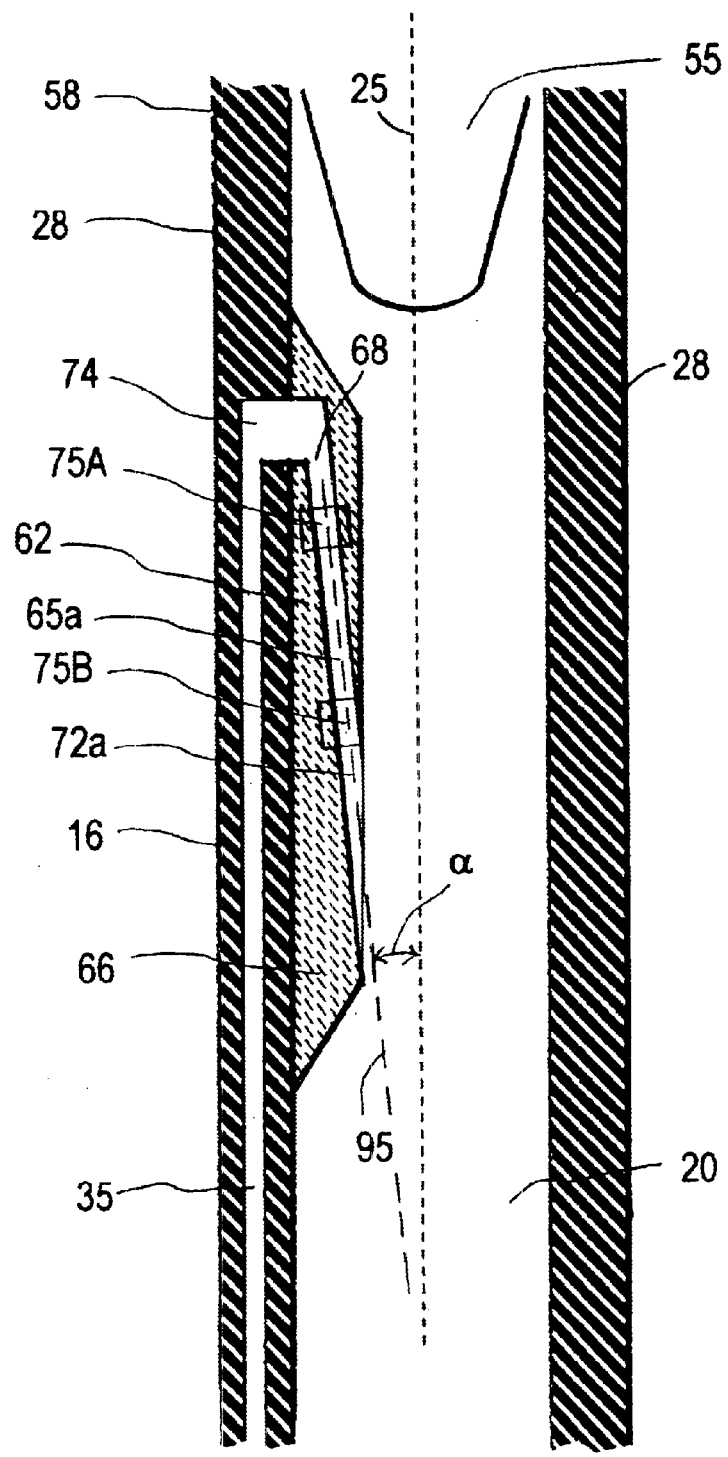
FIG. 13 is a view of alternative embodiment of a microchannel showing its axis relative to the axis of the extraction pathway taken along a line similar to line 9—9 of FIG. 8 rotated 90°.

The exemplary embodiment of FIG. 5 shows that a single channel body 62 is carried in working end 18 of catheter sleeve 16. Referring to FIG. 12, the system may also carry a plurality of channel bodies 62 (collectively) spaced apart over the length of the extraction pathway 20. This alternative system with multiple microchannel fluid jetting bodies is particularly suitable for very small diameter extraction pathways 20 wherein the multiple sets of channels thus cause fluid jets into the extraction channel to emulsify any particles entrained in the fluid flow along the entire length of the extraction pathway. The multiple locations of fluid jets into the pathway 20 further cause pressure differentials at a series of locations in the pathway 20 to enhance proximal-directed fluid flow within the pathway. In such a system, the electrical discharges in each channel body location can be contemporaneously timed by controller 82, with the same electrical leads then be adapted to deliver electrical energy to all channel bodies. Alternatively, the controller 82 can be programmed to deliver electrical energy sequentially over separate electrical to sequence electrical discharges between the channel bodies. As will be described below, the emulsification or ablation of embolic particles is caused by mechanical forces and thermal effects acting on the entrained particles. For this reason, the axis of the jetting effect from the open channel terminations 72a–72i may be directed inwardly to a certain extent toward the axis of pathway 20. As illustrated in FIG. 13, the jet axis or flow axis 95 may have an angle a relative to axis 25 of extraction pathway 20 ranging between about 0° and 45°. Preferably, the angle a between axis 25 of extraction pathway 20 and the flow axis of the channels range between about 0° and 30°. As another alternative, some channels may be substantially axially-aligned with the extraction pathway for accelerating fluid flows while other channels have axes at the angles described above for causing cavitation and emulsification of particles more centrally in the extraction pathway. In such an alternative embodiment, control circuitry may be provided for (i) causing a first electrical discharge repetition rate within the axially-aligned channels for maintaining the acceleration of fluid flows while, and (ii) causing a second discharge repetition rate within the angled channels for optimizing emulsification effects within the fluid flow.

Figure 14A:
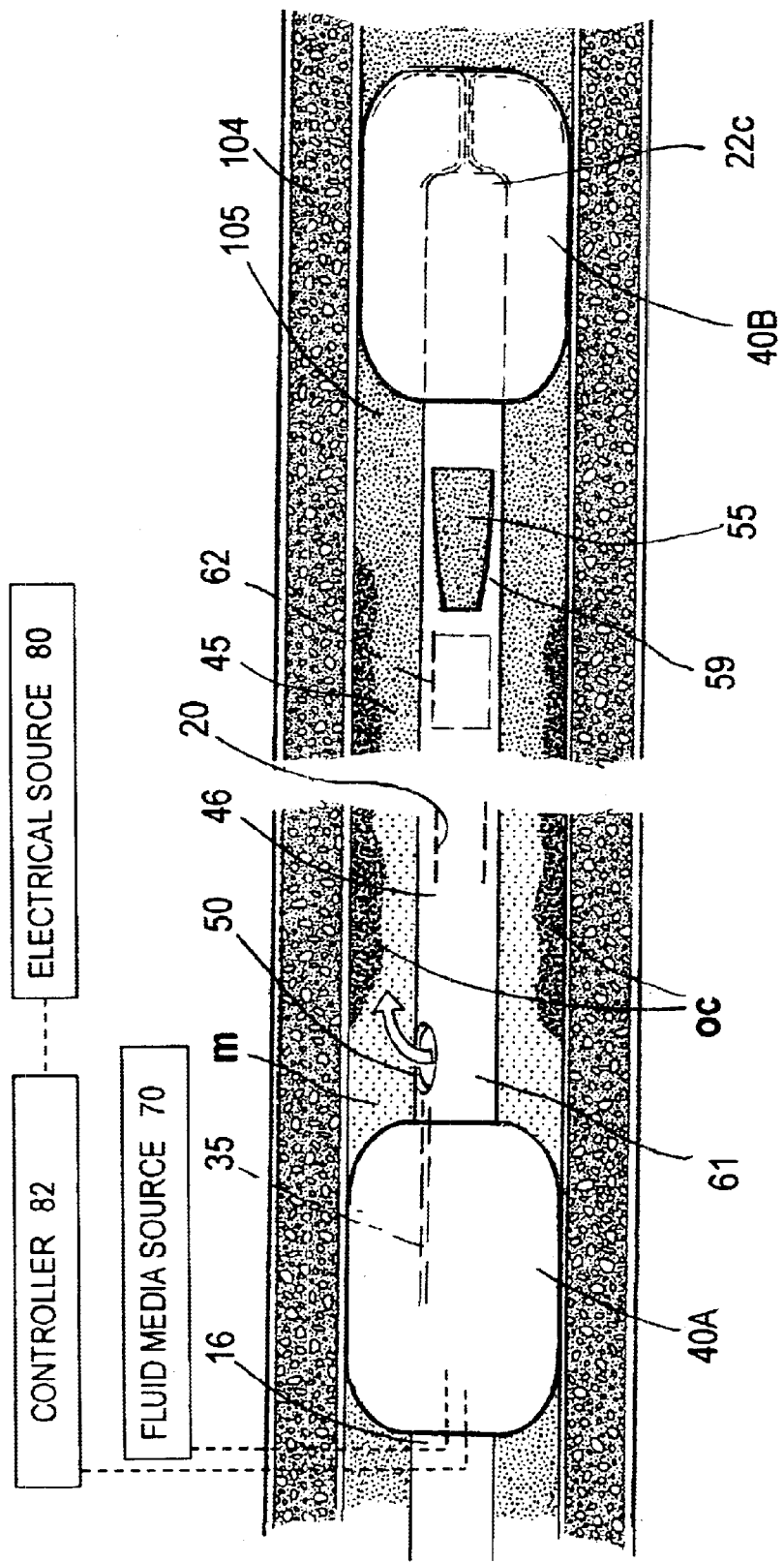
FIGS. 14A–14C are graphic representations of a steps of practicing the principles of the invention utilizing the deployed working end of FIG. 5.

III Method of Use of Type "A" Endovascular Intervention System for Extraction and Emulsification of Emboli In using the system to treat an occluded vascular graft, the patient would be prepared in the usual manner as in any interventional cardiology case and the working end 18 of the catheter system would be introduced to the targeted working space 45 in a patient's vasculature 100 under a suitable imaging system. Under such imaging, the working end 18 of the catheter is advanced with balloons 40A and 40B in the first collapsed position, typically over a guidewire 30, although the catheter tip could be closed with the catheter being advanced in a single operation without a guidewire. In FIGS. 5 & 14A, occlusive material oc is shown adhering to the vessel walls 104 around the targeted site. An objective of the method of the invention is to contain and remove occlusive materials, and the term occlusive material is used interchangeably herein with other terms more particularly identifying targeted materials that include any thrombus, calcified sclerotic materials, or other emboli, particles or fragments within any body lumen. Referring to FIG. 14A, after the working end 18 is in place, the guide wire is withdrawn entirely from bore 20 in the catheter sleeve 16 and the balloons 40A and 40B are inflated in the manner described above by delivering an inflation medium through common lumen 32 that expands both balloons. FIG. 14A shows distal balloon 40B in its second (expanded) position wherein the distal end 49b of balloon wall 48 over-rolls and substantially closes off the open distal termination 22c of bore 20 in the catheter sleeve.

FIG. 14A shows that the dual occlusion balloons engage vessel wall 104 thereby defining a working space 45 between the balloons that temporarily captures blood 105 therein. The next step of the method also is depicted in FIG. 14A wherein the physician introduces fluid media m through inflow lumen 35 under any suitable pressure (e.g., 1 to 25 psi at the handle 17) that thereafter flows through port 50 into working space 45. The controller 82 may be used to control the duration and pressure of such a fluid inflow with the purpose being to partially flush blood 105 from working space 45. The blood will naturally be forced through ports 55 into the extraction pathway 20. Without backpressure, the blood and introduced fluid can move proximally in pathway 20 to the catheter manifold 17 to exit the open proximal end 27 of the extraction pathway. This looped flow can carry the blood and fluid media m from the working space 45 without further assistance, but it should be appreciated that catheter system 15 also may include a negative pressure source (not shown) coupled to the open end 27 of pathway 20 to facilitate the initial low pressure circulation of fluid media m.

Figure 14B:
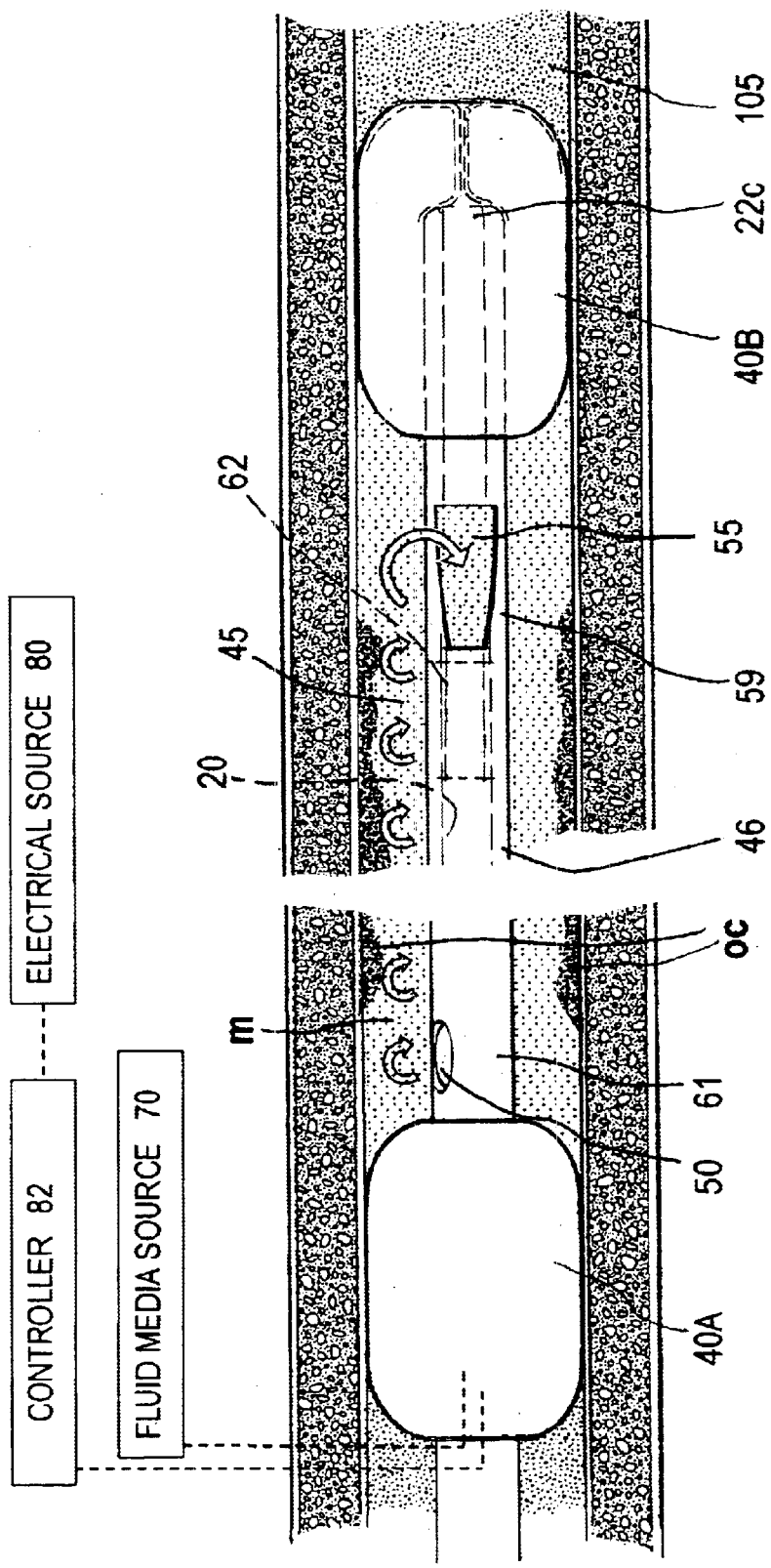
Figure 14C:
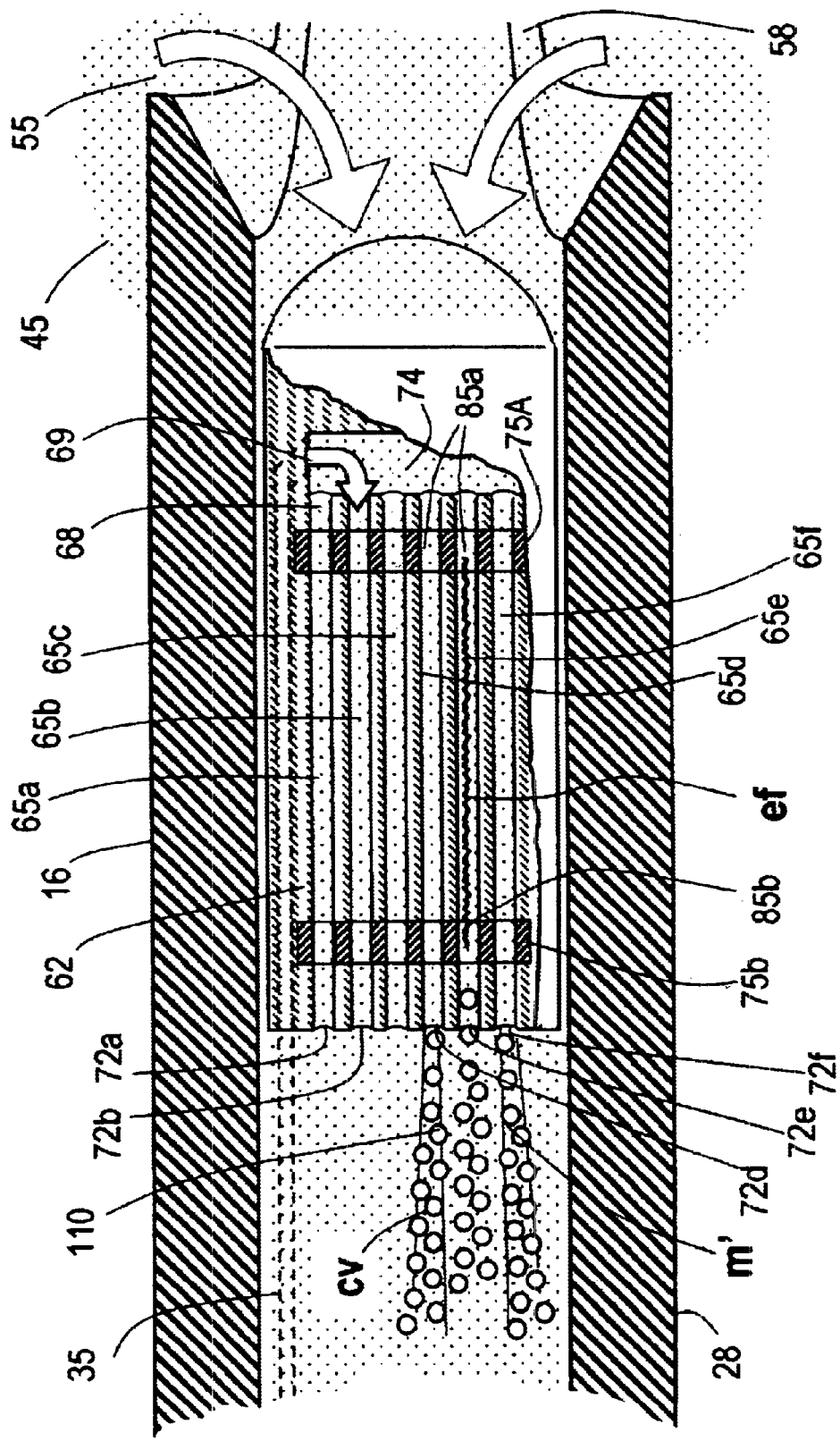

FIGS. 14B & 14C next depict graphic views of the working end 18 just after commencing a sequence of electrical discharges in the channels in cooperation with a selected fluid inflow rate of media m, to thereby accomplish the various aspects of the method of the invention contemporaneously, which include: (i) causing fluid turbulence in working space 45 to clean occlusive fragments oc or emboli from the vessel walls 104 as depicted in FIG. 14B; (ii) causing a pressure differential to thereby suction the fluid media m and occlusive material oc into the extraction pathway 20 as depicted in FIG. 14C; and (iii) emulsifying or ablating larger particles of occlusive materials oc entrained in the volume of fluid media m that is suctioned into and through the area of the fluid jets indicated 110 as also depicted in FIG. 14C.

Of particular interest, referring to FIG. 14C, the physician actuates controller 82 and electrical source 80 to deliver electrical energy to electrodes 75A and 75B at a selected power level and at a selected repetition rate. In order to further control the effect of electrical discharges in channels 65a–65i to create high velocity fluid flows, the fluid media m is selected from a class of biocompatible fluids, such as a saline solution, to have a known electrolytic component (i e., with known resistivity (Ohms/ml.), heat capacity (J/g.), etc.). Before initiation of an electrical discharge sequence, the fluid source 70 delivers fluid media m at a selected inflow pressure to lumen 35 at the catheter manifold as described above, with the flow rate optionally controlled by controller 82. After the electrical discharge sequence commences, the low inflow pressure may be maintained but preferably the fluid media m then flows inwardly in catheter sleeve 16 only as a result of the suction forces developed within extraction pathway 20 of the working end 18 by the pressure differential described above. For purposes of explanation, the sectional view of FIG. 14C graphically illustrates two discrete steps of the method of the invention. FIG. 14C shows the introduced fluid m flowing through inflow lumen 35 and chamber portion 74 to thereafter flow in the proximal direction within three channels (65a–65c) at the upper part of the drawing (see flow arrow 108). FIG. 14C also depicts electrical discharges (indicated graphically as electric field ef) within three channels (65d–65g) at the lower part of the drawing. It is these electrical discharges within channels 65d–65f that can cause a phase state change in a liquid media m to a gas phase media m' wherein the expansion of the media volume results in fluid jets 110 to exit the open terminations 72d–72f of channels 65d–65f. The fluid jets 110 of FIG. 14C thus cause high velocity flows in extraction pathway 20 to cause the differential pressures described above in the text accompanying FIG. 3. FIG. 14C is provided with arrows 120 that indicate the flow of fluid m from working space 45 at its ambient pressure around the working end through ports 55 and into the extraction pathway 20. FIG. 14C further graphically shows cavitation bubbles cv formed in the fluid jets 110 that will delivery energy to particles of occlusive materials oc (phantom view) entrained in the fluid flows that can emulsify or fragment such materials.

In practicing the method of the invention as depicted in FIG. 14C, the electrical source 80 of the invention is selected from a type known in the art for enabling fast sequences of brief, high intensity electrical discharges. As one example, the system can use an electrical generation source with a thyratron device for creating brief intense discharges. In other words, the system can generate a discharge pulse between first electrode 75A and second electrode 75B through the fluid media m that has flowed into each channel 65c–65f. The electrical source 80 is coupled to controller 82 that is programmed with suitable software to independently modulate all operational parameters of the energy levels and time intervals of the electrical discharges, including: (i) voltage, current and peak electrical power delivery per discharge; (ii) the length of a discharge; (iii) the profile of energy within each discharge or pulse, and (iv) the repetition rate of discharges resulting in a set or variable discharge rate.

As described above, FIG. 14C depicts the ejection or jetting of fluid media m as the media is transiently vaporized by the electrical discharge (field ef) thus undergoing an ultra-rapid or explosive liquid to gas transformation (i.e., from liquid media m to gas media m') within the channels caused by the electrical discharge between the electrodes 75A and 75B. It is calculated that attainable fluid velocities within extraction pathway 20 will be in the range from about 0.5 m/s to 25 m/s. More preferably, the system can provide fluid velocities within extraction pathway 20 in the range from about 1 m/s to 10 m/s. The jetting from the open terminations 72a–72f of channels 65a–65f in FIG. 14C will occur naturally as the back pressure from fluid source 70 on media m in the system will prevent any reverse flows.

One important aspect of the invention relates to removing occlusive material oc from the working space 45. As can be understood from FIG. 14C, the jetting of fluid media m into extraction pathway 20 causes the fluid pressure differentials that suction the fluid media from port 50 into and through the working space 45 as depicted in FIG. 14B. The circulation of fluid m through working space 45 will be substantially turbulent as indicated generally by arrows 125. It is believed that this turbulent circulatory flow can be made more or less turbulent by adjusting the repetition rate and other parameters of the electrical discharge sequence as well as the media m inflow rate, since such adjustments will essentially pulse or surge the fluid inflows from port 50 into working space 45. It is believed that this controllable aspect of the invention will allow the turbulent flows 125 to scour and cleanse the vessel walls around the working space 45 of occlusive materials oc.

Still referring to FIG. 14B, the electrical discharges also maintain fluid flows along with entrained occlusive material oc within the pathway 20 from the working end 15 to the catheter handle. For very small diameter fluid extraction pathways 20, the system may be provided with a plurality of spaced apart channel structures 62 as shown in As FIG. 12. Sequential or contemporaneous electrical discharges in the spaced apart channel structures 62 (collectively) can maintain or enhance fluid velocity along the entire length of the extraction pathway.

FIGS. 14B & 14C also help explain how the electrical discharge system of the invention is adapted for emulsification or fragmentation of occlusive materials oc to insure of minimally sized particles that can be easily entrained in the fluid flow in extraction pathway 20. It is postulated that the energy parameters of the electrical discharge sequence can be modulated to produce cavitation bubbles cv of a selected dimension in fluid media that is proximate to the open terminations 72a–72f of channels 65a–65f to deliver mechanical energy in the form of strong acoustic waves to the fluid media. The creation and collapse of such cavitation bubbles cv can emulsify or fragment any occlusive particle oc captured in the froth of the jets 110. The electrical discharge system of the invention also delivers thermal energy to media proximate to the open terminations of channels 65a–65f that can ablate or emulsify particles entrained in the media m. If such thermal energy is desired, the electrode 75B are preferably located close to the open terminations 72a–72f of the channels (see FIG. 14C). Further, the system can easily deliver chemical energy to fluid media proximate to channel terminations 72a–72f by providing any suitable pharmacological agent (e.g., t-PA, streptokinase or urokinase) within fluid media m introduced from source 70 for dissolving occlusive material similar to the manner disclosed in co-pending U.S. patent application Ser. No. 09/181,206 filed Oct. 28, 1998, which in incorporated herein by this reference.

The system disclosed herein can be tested with the modulation of all electrical discharge parameters to define the optimal repetition rate to emulsify embolic materials. Initial modeling suggests that discharge repetition rates may range from about 1 Hz to 2 kHz. More preferably, the discharge repetition rates range from about 10 Hz to 1 kHz. The energy required for fluid vaporization of fluid media m and jetting from channels 65a–65f is entirely dependent on the diameter of microchannels and can be determined by testing. It is postulated that the electrical discharge system described above can generate pressure differentials at ports 55 that exceed 1 atmosphere, and may range from about 0.1 atmosphere to about 2.0 atmospheres, and such pressures will suction the fluid volume and occlusive materials rapidly from working space 45.

Of particular interest, the system of the invention cannot cause overpressures in the working space 45 since there is not a remote pressure source pumping fluid media m into the working space. The system only provides suction forces that are completely contained within the central extraction passageway 20 of the catheter during it operation. These suction forces then can draw the fluid media m from source 70.

IV. Construction of Type "B" Endovascular Intervention System for Extraction of Embolic Particles Referring to FIGS. 15A & 15B, the working end of a Type "B" catheter system 215 corresponding to the invention is shown. The system again has a thin-wall catheter sleeve 216 that extends to a distal working end 218 with a central extraction channel 220. The electrical discharge system for causing high velocity fluid flows within the extraction channel 220 is the same as described previously. The Types "B" embodiment differs from the Type "A" embodiment in two ways: (i) the working end 218 of the Type "B" system includes an additional channel 224 in the catheter sleeve 216 for blood perfusion around the occlusion balloons; and (ii) the working surface 46 of the catheter sleeve between the occlusion balloons (optionally) carries additional interventional functionality-in this case a balloon-deployed stent 225.

Figure 15A:
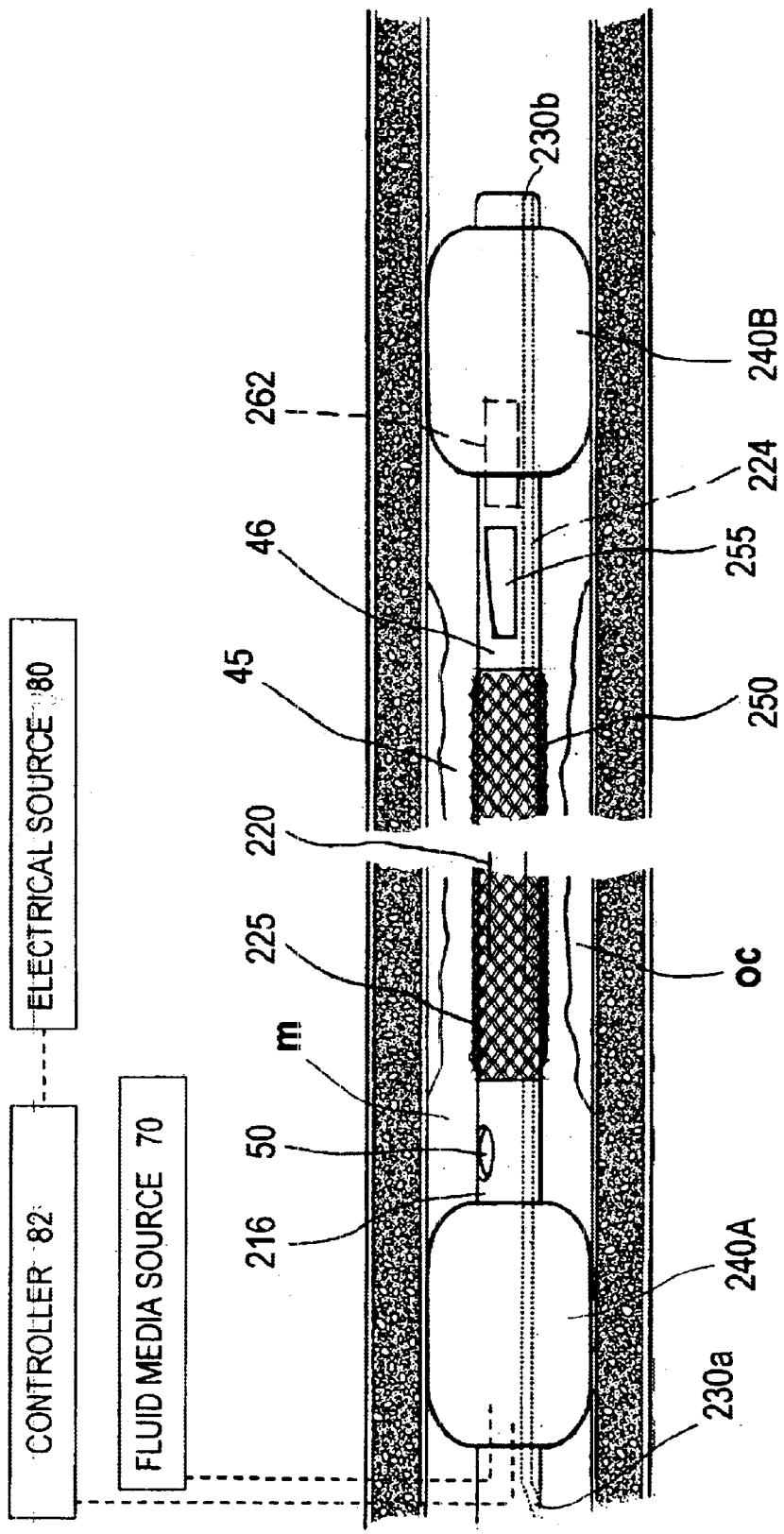
FIG. 15A is view of a Type "B" catheter working end that is deployed within a targeted vessel, the exemplary embodiment carrying a stent delivery system between the paired occlusion balloons.
Figure 15B:
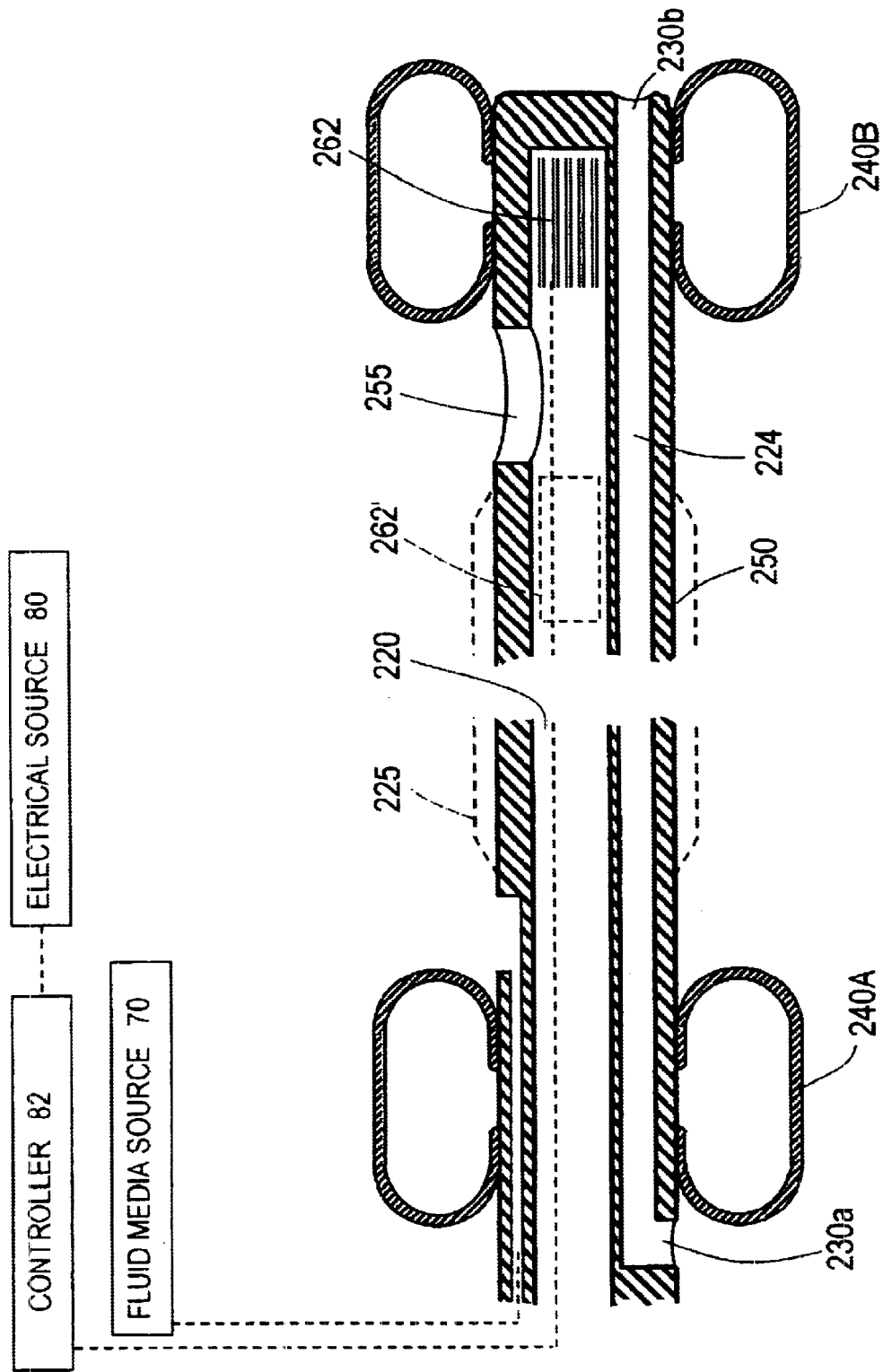
FIG. 15B is a sectional view of the working end of FIG. 15A showing a blood perfusion channel within the catheter working end.

FIG. 15B shows that wall 228 of catheter sleeve 216 carries a perfusion channel 224 that extends from a proximal open end 230a in the surface of the catheter sleeve to a distal open end 230b, the open ends on either side of the occlusion balloon system. In this embodiment, the central extraction channel 220 has a closed distal termination 233 so that the system is adapted for single operation introduction without a guidewire, or additional structure can be carried by the working end (as in rapid exchange catheters known in the art) for using the working end 218 with a guidewire. As can be seen by graphically by arrows 235 in the not-to-scale illustration of FIG. 15B, blood 105 can flow through channel 224 around the first and second occlusion balloons 240A and 240B. In this embodiment, the microchannel structure 262 is located slightly at distal from ports 255 that communicate with extraction channel. The microchannel structure indicated at 262' (phantom view) illustrates an optional location for the energy delivery system that compares with the Type "A" embodiment.

It can be understood from FIG. 15A that stent 225 can be expanded by central balloon 250 that communicates with a remote fluid source via another lumen (not shown) in the catheter sleeve. The manner of deploying the stent 225 often will cause occlusive materials oc to be dislodged from the vessel walls. By operating the electrical discharge system of the invention following, or contemporaneous with, stent deployment, the occlusive material oc can be captured and removed through ports 255 as described above. While a stent deployment system is shown in FIGS. 15A & 15B, it should be appreciated that the optional interventional functionality also can comprise an angioplasty balloon system, an atherectomy cutting system or any other type of occlusion removal or ablation system.

The exemplary embodiments described above are provided with a fluid media source that comprises a biocompatible liquid media, wherein the electrical discharges in such a media causes a phase state change or vaporization of the fluid media to cause an increase in the media volume thereby creating the high velocity flows. It should be appreciated the fluid media may be any liquid or gas that poses no substantial risk to the patient when used in the manners described above. A suitable gas can be any gas that expands in volume following an electrical discharge, in combination with oxygen for example, and can be hydrogen in microvolumes within a microchannel structure. The gas expansion then would be characterized as an ultrafast event caused by chemical energy release.

The system has been described above for use in endovascular interventions. However, it should be appreciated that a similar system can be used in any body lumen or duct (e.g., ureter, bile ducts, etc.) to cause removal and emulsification of occlusive materials.

Those skilled in the art will appreciate that the exemplary embodiments and descriptions thereof are merely illustrative of the invention as a whole, and that variations in controlling the duration of intervals of energy delivery, in controlling the repetition rate, and in controlling the voltage applied to the electrode arrangement may be made within the spirit and scope of the invention. Specific features of the invention may be shown in some figures and not in others, and this is for convenience only and any feature may be combined with another in accordance with the invention. While the principles of the invention have been made clear in the exemplary embodiments, it will be obvious to those skilled in the art that modifications of the structure, arrangement, proportions, elements, and materials may be utilized in the practice of the invention, and otherwise, which are particularly adapted to specific environments and operative requirements without departing from the principles of the invention. The appended claims are intended to cover and embrace any and all such modifications, with the limits only of the true purview, spirit and scope of the invention.

What is claimed is:

1. A medical catheter for treating an endoluminal site, comprising:
    a catheter member defining an interior bore surrounded by a catheter wall;
    at least one channel carried in a wall portion of the catheter member;
    wherein each said channel carries spaced apart first and second electrodes, each channel having an open termination directed proximally to communicate with said interior bore; and
    an electrical source operatively coupled to the first and second electrodes.

2. The system of claim 1 wherein each said channel has a cross-sectional dimension ranging from about 0.5 $\mu$m to 2000 $\mu$m.

3. The system of claim 1 wherein each said channel has a cross-sectional dimension ranging from about 1 pm to 1000 $\mu$m.

4. The system of claim 1 wherein each said channel has a cross-sectional dimension ranging from about 5 $\mu$m to 500 $\mu$m.

5. The system of claim 1 further comprising first and second spaced apart balloons carried on the catheter member.

6. The system of claim 1 further comprising a fluid pathway in the catheter wall that communicates with an end of each channel that opposes the open termination thereof.

7. The system of claim 1 further comprising a remote fluid media source coupled to a proximal end of said fluid pathway.

8. The system of claim 7 wherein the electrical source provides electrical discharges within said fluid media disposed between the first and second electrodes to cause fluids to exit said open termination at a velocity ranging from about 0.25 m/s to 25 mis.

9. The system of claim 7 wherein the electrical source provides electrical discharges within said fluid media disposed between the first and second electrodes to cause fluids to exit said open termination at a velocity ranging from about 1 m/s to 10 m/s.

10. The system of claim 7 wherein the fluid media has a sped resistivity.

11. The system of claim 1 wherein an axis of each said channel is angled relative to an axis of the interior bore between about 0° and 45°.

12. The system of claim 1 wherein an axis of each said channel is angled relative to an axis of the interior bore between about 0° and 30°.

13. The system of claim 1 further comprising a controller coupled to the electrical source for controlling the parameters of electrical discharges selected from the class consisting of power delivery in a discharge, profile of energy delivery within a discharge, length of a discharge and repetition rate of discharges.

14. The system of claim 13 wherein the repetition rate is from 1 Hz to 2000 Hz.

15. The method of claim 13 wherein the repetition rate is from 10 Hz to 1000 Hz.

* * * * *